United States Patent
Suzuki et al.

(10) Patent No.: US 10,675,191 B2
(45) Date of Patent: Jun. 9, 2020

(54) ABSORBENT ARTICLE WITH LIQUID IMPERMEABLE SURFACE SHEET PORTION

(71) Applicant: DAIO PAPER CORPORATION, Shikokuchuo-shi, Ehime (JP)

(72) Inventors: Migaku Suzuki, Chigasaki (JP); Yoshio Hirai, Tokyo (JP)

(73) Assignee: DAIO PAPER CORPORATION, Shikokuchuo-shi (JP)

( * ) Notice: Subject to any disclaimer, the term of this patent is extended or adjusted under 35 U.S.C. 154(b) by 797 days.

(21) Appl. No.: 14/428,838

(22) PCT Filed: Sep. 24, 2012

(86) PCT No.: PCT/JP2012/074394
§ 371 (c)(1),
(2) Date: Mar. 17, 2015

(87) PCT Pub. No.: WO2014/045439
PCT Pub. Date: Mar. 27, 2014

(65) Prior Publication Data
US 2015/0230997 A1    Aug. 20, 2015

(51) Int. Cl.
*A61F 13/494*        (2006.01)
*A61F 13/513*        (2006.01)

(52) U.S. Cl.
CPC .... *A61F 13/49413* (2013.01); *A61F 13/4942* (2013.01); *A61F 13/49453* (2013.01); *A61F 13/51305* (2013.01)

(58) Field of Classification Search
CPC ............... A61F 13/512; A61F 13/5126; A61F 13/51305; A61F 2013/51147;
(Continued)

(56) References Cited

U.S. PATENT DOCUMENTS 3,888,254 A * 6/1975 Hendricks ........... A61F 13/4755
                                                  604/387
4,015,604 A * 4/1977 Csillag ................ A61F 13/4755
                                                  604/365
(Continued)

FOREIGN PATENT DOCUMENTS

EP    1166729 A1 *  1/2002  ....... A61F 13/49413
EP    2886091 A1    6/2015
(Continued)

OTHER PUBLICATIONS

Cover definition, 2016, American Heritage(R) Dictionary of the English Language, Houghton Mifflin Publishing Company, 6th Edition.*
(Continued)

*Primary Examiner* — Kathryn E Ditmer
(74) *Attorney, Agent, or Firm* — Oliff PLC

(57) ABSTRACT

An absorbent article including: a leak preventer sheet form; an absorber capable of absorbing bodily fluid, wherein minimum one layer is above the leak preventer; a surface sheet covers part of the absorber upper surface and includes a liquid impermeable area; right and left floating leg gathers above the absorber, from front to rear end parts in length direction of the absorbent article body via a front body, a crotch part and rear body, wherein floating leg gather has a head and hanging parts connects to the head part, wherein a front and rear end parts of the floating leg gather are respectively coupled to the front and rear end parts vicinity of the absorbent article body, the hanging part hanging from the head part toward the absorber; wherein a transferring passage is formed by coupling each hanging part of the right and left floating leg gathers to the surface sheet.

12 Claims, 15 Drawing Sheets

Figure 1:
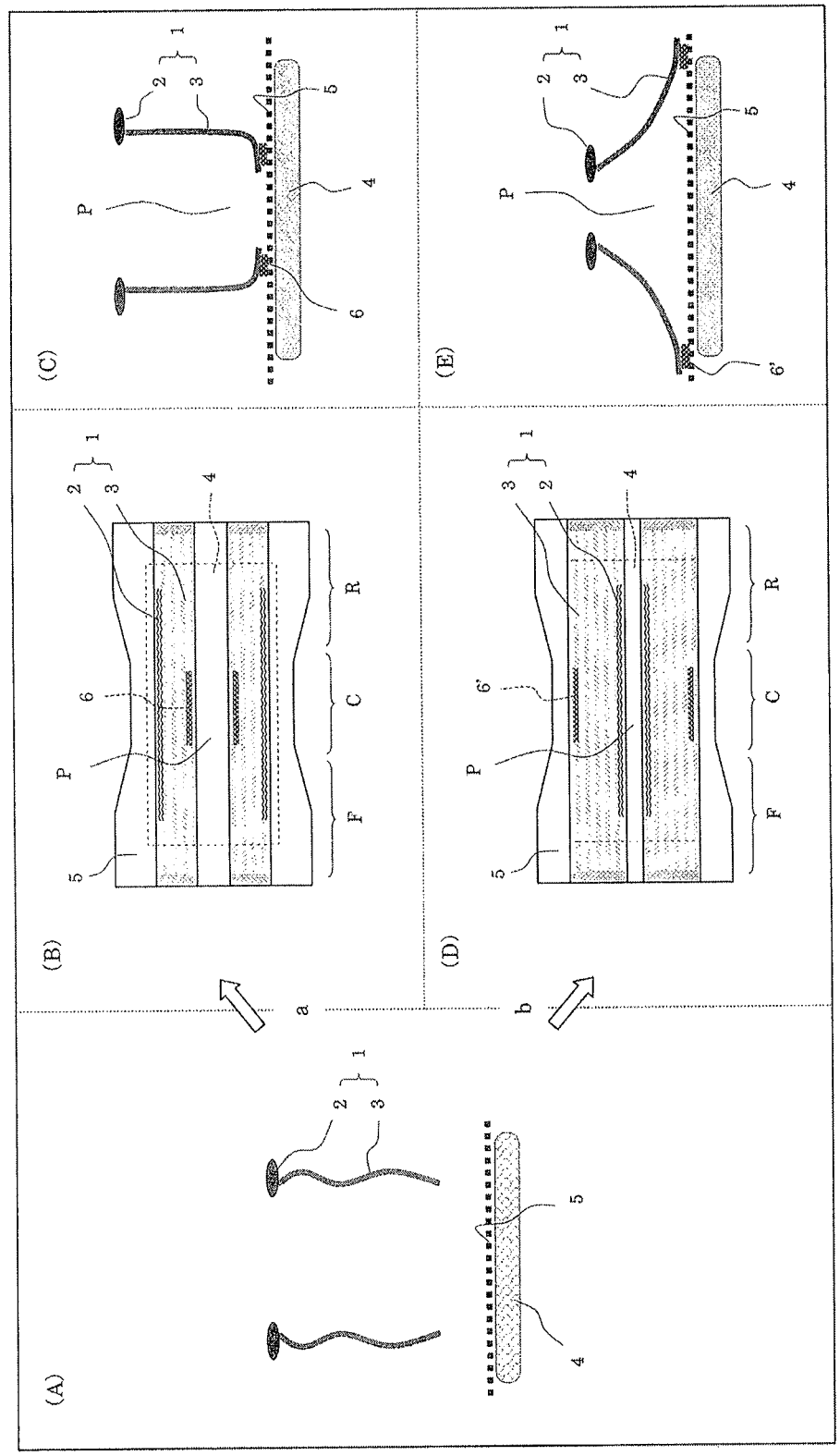

(58) Field of Classification Search
CPC .......... A61F 2013/5128; A61F 13/4752; A61F 13/4755; A61F 2013/425
USPC .................................................. 604/385.28
See application file for complete search history.

(56) References Cited

U.S. PATENT DOCUMENTS

| | | | | |
|---|---|---|---|---|
| 4,704,116 A * | 11/1987 | Enloe | ................ | A61F 13/49009 604/358 |
| 4,795,454 A * | 1/1989 | Dragoo | ............. | A61F 13/49009 604/378 |
| 4,808,177 A | 2/1989 | DesMarais et al. | | |
| 4,900,317 A * | 2/1990 | Buell | ................ | A61F 13/49009 604/370 |
| 5,023,124 A * | 6/1991 | Kobayashi | ............ | A61F 13/512 428/138 |
| 5,292,316 A * | 3/1994 | Suzuki | ................. | A61F 13/505 604/358 |
| 5,304,159 A * | 4/1994 | Tanji | ................. | A61F 13/49473 604/358 |
| 5,304,160 A * | 4/1994 | Igaue | ................ | A61F 13/49009 604/358 |
| 5,370,634 A * | 12/1994 | Ando | ................ | A61F 13/49009 604/358 |
| 5,397,318 A * | 3/1995 | Dreier | ................ | A61F 13/49009 604/385.19 |
| 5,582,606 A * | 12/1996 | Bruemmer | .......... | A61F 13/4942 604/373 |
| H001630 H * | 1/1997 | Roe | ............................ | 604/385.28 |
| 5,607,416 A * | 3/1997 | Yamamoto | ............. | A61F 13/49 604/385.27 |
| 5,624,424 A * | 4/1997 | Saisaka | ............. | A61F 13/49011 604/385.28 |
| 5,662,637 A * | 9/1997 | Kitaoka | ............... | A61F 13/4942 604/385.28 |
| 5,672,166 A * | 9/1997 | Vandemoortele | ............................ | A61F 13/15756 156/164 |
| 5,722,969 A * | 3/1998 | Ito | ........................... | A61F 13/58 604/386 |
| H001746 H * | 8/1998 | Carrier | .................... | A61F 13/15 604/385.23 |
| 5,817,079 A * | 10/1998 | Bergquist | .......... | A61F 13/15626 428/299.1 |
| 5,843,067 A * | 12/1998 | Trombetta | .......... | A61F 13/4752 604/385.23 |
| 5,899,894 A * | 5/1999 | Palumbo | ............ | A61F 13/49017 604/378 |
| 5,921,975 A * | 7/1999 | Suzuki | ............... | A61F 13/47245 604/385.04 |
| 5,990,375 A * | 11/1999 | Lindquist | .......... | A61F 13/15699 604/378 |
| 6,102,892 A | 8/2000 | Putzer et al. | | |
| 6,120,488 A * | 9/2000 | VanRijswijck | ....... | A61F 13/494 604/364 |
| 6,159,191 A * | 12/2000 | Mishima | ........... | A61F 13/49426 604/385.28 |
| 6,217,890 B1 * | 4/2001 | Paul | ................. | A61F 13/15203 424/402 |
| 6,229,063 B1 * | 5/2001 | Shimoe | ................ | A61F 13/42 604/378 |
| 6,320,096 B1 * | 11/2001 | Inoue | ................ | A61F 13/51305 604/378 |
| 6,476,288 B1 * | 11/2002 | VanRijswijck | ....... | A61F 13/494 604/359 |
| 6,585,712 B2 * | 7/2003 | Yoshimasa | ............ | A61F 13/472 604/385.27 |
| 6,613,955 B1 * | 9/2003 | Lindsay | ............. | A61F 13/4704 604/378 |
| 6,616,646 B2 * | 9/2003 | Wada | ................. | A61F 13/4752 604/385.101 |
| 6,648,869 B1 * | 11/2003 | Gillies | ............... | A61F 13/51104 604/385.101 |
| 6,706,029 B1 * | 3/2004 | Suzuki | ............... | A61F 13/49009 604/385.01 |
| 6,706,030 B1 * | 3/2004 | Okuda | ............... | A61F 13/49413 604/385.24 |
| 6,716,205 B2 * | 4/2004 | Popp | ................... | A61F 13/49413 604/378 |
| 6,767,343 B2 * | 7/2004 | Shimada | ............. | A61F 13/49017 604/385.25 |
| 7,189,219 B1 * | 3/2007 | Kasai | ..................... | A61F 13/494 604/385.24 |
| 7,524,312 B2 * | 4/2009 | Onishi | ............... | A61F 13/49426 604/385.101 |
| 7,666,173 B2 * | 2/2010 | Mishima | ............... | A61F 13/4915 604/385.101 |
| 7,763,001 B2 * | 7/2010 | Kawamura | ......... | A61F 13/4752 604/385.09 |
| 7,763,004 B2 * | 7/2010 | Beck | ................. | A61F 13/49426 604/358 |
| 7,824,385 B2 * | 11/2010 | Ecker | .................... | A61F 13/475 604/361 |
| 7,976,523 B2 * | 7/2011 | Suzuki | ................... | A61F 13/512 604/385.101 |
| 9,539,152 B2 * | 1/2017 | Suzuki | ................ | A61F 13/4942 |
| 9,782,304 B2 * | 10/2017 | Suzuki | ............... | A61F 13/49015 |
| 2001/0021834 A1 * | 9/2001 | Yoshimasa | ............ | A61F 13/472 604/385.01 |
| 2002/0022114 A1 * | 2/2002 | Sorensen | ............... | A61F 13/475 428/190 |
| 2002/0058920 A1 * | 5/2002 | Toyoda | ............. | A61F 13/49011 604/385.28 |
| 2002/0138060 A1 * | 9/2002 | Nakaoka | .............. | A61F 13/4942 604/385.25 |
| 2003/0023225 A1 * | 1/2003 | Sayama | .............. | A61F 13/49426 604/385.28 |
| 2003/0100872 A1 | 5/2003 | Roe et al. | | |
| 2004/0002690 A1 * | 1/2004 | Miyamoto | ........ | A61F 13/49017 604/385.25 |
| 2004/0039363 A1 * | 2/2004 | Sugiyama | ......... | A61F 13/49473 604/385.101 |
| 2004/0059309 A1 | 3/2004 | Nortman | | |
| 2004/0176733 A1 * | 9/2004 | Glaug | .................... | A61F 13/534 604/378 |
| 2004/0265533 A1 * | 12/2004 | Hoying | ............. | A61F 13/51121 428/92 |
| 2005/0113790 A1 * | 5/2005 | Suzuki | ................ | A61F 13/4752 604/385.28 |
| 2006/0058769 A1 * | 3/2006 | Suzuki | ................ | A61F 13/512 604/385.101 |
| 2007/0032772 A1 | 2/2007 | Ehrnsperger et al. | | |
| 2007/0073259 A1 * | 3/2007 | Erdman | ............. | A61F 13/4942 604/385.28 |
| 2007/0088306 A1 | 4/2007 | Sugiyama et al. | | |
| 2008/0294138 A1 * | 11/2008 | Andersson | ........ | A61F 13/15203 604/385.23 |
| 2009/0005752 A1 * | 1/2009 | Suzuki | ................ | A61F 13/494 604/385.101 |
| 2009/0036852 A1 | 2/2009 | Suzuki et al. | | |
| 2011/0106040 A1 | 5/2011 | Minato et al. | | |
| 2012/0123365 A1 * | 5/2012 | Pan | ....................... | A61K 8/0208 604/367 |
| 2015/0080828 A1 * | 3/2015 | Suzuki | ................ | A61F 13/4942 604/385.01 |
| 2015/0190289 A1 * | 7/2015 | Suzuki | ............... | A61F 13/49413 604/385.101 |
| 2015/0216738 A1 * | 8/2015 | Suzuki | ............... | A61F 13/49473 604/385.19 |

FOREIGN PATENT DOCUMENTS

| | | |
|---|---|---|
| JP | 5317362 A | 12/1993 |
| JP | 2000288012 A | 10/2000 |
| JP | 2005287662 A | 10/2005 |

(56) References Cited

FOREIGN PATENT DOCUMENTS

| JP | 2009502407 A | 1/2009 |
| JP | 2011000279 A | 1/2011 |
| WO | 2009119135 A1 | 10/2009 |

OTHER PUBLICATIONS

Dec. 4, 2012 International Search Report issued in International Patent Application No. PCT/JP2012/074394.
Apr. 12, 2016 Extended Search Report issued in European Patent Application No. 12885022.9.
Dec. 4, 2012 Written Opinion issued in International Patent Application No. PCT/JP2012/074394.
Dec. 4, 2012 Office Action issued in Japanese Patent Application No. 2012-543383.

* cited by examiner (A)

(B)

(A)

(B)

(C)

(A)

(B)

(C)

(D)

(A)

(B)

(A)

(B)

(A)

(B)

(A)

(B)

(C)

(A)

(B)

(C)

(D)

(E)

(A)

(B)

ABSORBENT ARTICLE WITH LIQUID IMPERMEABLE SURFACE SHEET PORTION

FIELD OF THE INVENTION

The present invention relates to an absorbent article provided with novel leg gathers.

BACKGROUND ART

Absorbent articles such as paper diapers (for infants and adults), sanitary napkins, incontinence articles, training pants or the like are articles that absorb bodily fluids, such as urine excreted from a wearer, by means of an absorber that makes use of a super absorbent polymer (hereinafter referred to as an "SAP"), fluffy pulp or the like.

Conventional absorbent articles prevent leakage by closely attaching an absorber to the surface of the body of a wearer without any gap and by transferring the excreted bodily fluids from the surface of the absorber to the inside thereof to be absorbed therein.

Such closely-attached state of the absorber to the body of the wearer is achieved by applying a "pressing force from the exterior" to the absorber. This will be described in more detail by taking an infant's diaper as an example.

In infant's diapers, as a means for generating a "pressing force from the exterior," various stretchable materials (similar to those used in pantyhose, supporters, competition swimsuits and the like) are arranged at various parts. Especially in recent years, for tapeless underpants-type diapers which have become a main trend for infant' diapers, since they are mainly intended for infants when their body movement becomes active (approximately 6 kg or more in body weight), it is necessary to make use of a stretchable material.

In general, the following stretchable materials are used for underpants-type diapers:
(1) A waist gather band (waist part stretchable body): the waist gather band serves as a fixing band that connects a front end part and a rear end part of a diaper body to each other, attaches the diaper closely around the waist and prevents the diaper from sliding down;
(2) Shirring gathers or trunk gathers (trunk part maintaining stretchable body): the shirring or trunk gathers are present so as to cover each of a back surface and a ventral surface of the diaper and exhibit functions of pressing the absorber in the vicinities of the back surface and the ventral surface against the surface of the wearer's body; and
(3) Leg gathers (leg part stretchable body): the leg gathers provide sealing, in the vicinity of the crotch part, so that no gap is formed between the diaper body and the wearer's body and play a role of a dam (bank) that prevents leakage from the side surfaces of the absorber. The leg gathers are classified into the following three types depending on their roles, and each type may be used alone or two or more types may be used in combination.
(3a) First inner leg gather (ILG): the first ILG is provided above the absorber or on a side edge of the absorber, includes a stretchable head part and a leg part made of a non-woven fabric, and usually has a standing geometry.
(3b) Second inner leg gather (ILG): the second ILG is provided on the side edge of the absorber or on the exterior thereof, includes a stretchable head part and a leg part made of a non-woven fabric, and usually has a standing geometry.
(3c) Outer leg gather (OLG) or gusset gather: the OLG or gusset gather is provided by sandwiching a stretchable material by a top sheet and a leak preventer from both side surfaces at the side edge of the diaper body, and it is usually flat; however, it is, in some cases, folded on the inward side and is used in a standing geometry.

SUMMARY OF THE INVENTION

Problems to be Solved by the Invention

When the above-described stretchable materials are used in a form where a strong tension concentrates, as in a wide rubber band, they give the wearer a feeling of restraint and leave marks, and thus, improvement efforts have been made such as to arrange, in general, a plurality of fine polyurethane filaments in parallel to disperse tension. However, current diapers are still greatly associated with a feeling of restraint for the wearer, both physically and psychologically.

In addition, since conventional diapers achieve the closely-attached state of the absorber to the wearer's body by a "pressing force from the exterior," hot and stuffy state and rashes are likely to occur.

Accordingly, it is an object of the present invention to provide an absorbent article that has less of a feeling of restraint at the time of wearing and in which the occurrence of hot and stuffy state and rashes is suppressed.

Means for Solving the Problems

In order to achieve the object set forth above, the present inventors contemplated achieving an absorbent article that has less of a feeling of restraint at the time of wearing and in which the occurrence of hot and stuffy state and rashes is suppressed, by means of a new concept, without using a "pressing force from the exterior."

As a result of diligently conducting research, the present inventors have found that: after providing a surface sheet that covers at least part of an upper surface of an absorber and that includes a liquid impermeable area at least part thereof, by providing a pair of right and left floating leg gathers (hereinafter referred to as "FLGs"), which include head parts and hanging parts that connect to the head parts and which are configured such that a front end part and a rear end part of the FLG are respectively coupled to the vicinity of a front end part and the vicinity of a rear end part of the absorbent article body and such that the hanging parts hang down from the head parts toward the absorber, as a pair of FLGs arranged, above the absorber, from a front end part to a rear end part of the absorbent article body in the length direction via a front body, a crotch part and a rear body; and by coupling each of the hanging parts of the pair of right and left FLGs to the surface sheet such that a transferring passage for bodily fluids is formed by such hanging parts and the surface sheet, the FLGs and the absorber are spaced apart at the time of wearing the absorbent article, and thus, a feeling of restraint at the time of wearing is reduced and contact of the urine or feces excreted onto the absorber with the wearer's skin is effectively suppressed and thus, the occurrence of hot and stuffy state and rashes is suppressed, and then completed the present invention.

The present invention focuses especially on a skin contact member and an absorber member, among the members configuring the absorbent article.

(1) In the conventional absorbent article, both the absorber and the gather that stands up therefrom are pressed against the wearer's skin, whereas in the present invention, a "skin contact member which functions by being constantly and closely attached in a soft manner to the skin of the wearer on the side edges of the bodily fluid excretory organ" and an "absorber member which is rigid and requires a form retaining property" are functionally separated;

(2) the above-described "absorber member" is physically spaced apart from the surface of the wearer's body; and (3) in regard to the above-described "skin contact member," a pair of FLG s having a pair of right and left head parts and a pair of right and left hanging parts that hangs down from the head parts toward the absorber member, are provided as a separate entity.

Based on the above, the present invention is to provide a new absorbent article in which the absorber is not pressed against the wearer's body surface like in the conventional absorbent article and which is capable of sufficiently fulfilling the absorption function of the absorber in the condition where the absorber is kept spaced apart from the wearer's body surface.

Namely, the present invention provides the following (1) to (12):

(1) An absorbent article including:
a leak preventer in sheet form;
an absorber capable of absorbing a bodily fluid, wherein at least one layer thereof is arranged above the leak preventer;
a surface sheet that covers at least a part of an upper surface of the absorber and that includes a liquid impermeable area at least a part thereof; and
a pair of right and left floating leg gathers that are arranged, above the absorber, from a front end part to a rear end part in a length direction of a body of the absorbent article via a front body, a crotch part and a rear body,
wherein the floating leg gather has a head part and a hanging part that connects to the head part,
wherein a front end part and a rear end part of the floating leg gather are respectively coupled to the vicinity of the front end part and the vicinity of the rear end part of the body of the absorbent article, the hanging part hanging down from the head part toward the absorber; and
wherein a transferring passage for bodily fluids is formed by coupling each of the hanging parts of the pair of right and left floating leg gathers to the surface sheet.

(2) The absorbent article according to (1),
wherein the pair of right and left floating leg gathers are arranged such that both the head parts face outward and both the hanging parts face inward,
wherein the hanging parts of the pair of right and left floating leg gathers are arranged opposite to each other with a space therebetween, and
wherein the surface sheet is present between coupling parts of the hanging parts of the pair of right and left floating leg gathers and the surface sheet.

(3) The absorbent article according to (1),
wherein the pair of right and left floating leg gathers are arranged such that both the head parts face inward and both the hanging parts face outward,
wherein the head parts of the pair of right and left floating leg gathers are arranged opposite to each other with a gap therebetween, and
wherein the surface sheet is present between coupling parts of the hanging parts of the pair of right and left floating leg gathers and the surface sheet.

(4) The absorbent article according to any of (1) to (3),
wherein a center part of the surface sheet in the lateral direction is the liquid impermeable area, and
wherein right and left sides of the liquid impermeable area of the surface sheet are liquid permeable areas, and
wherein the hanging parts of the pair of right and left floating leg gathers are respectively coupled to the vicinities of right and left edge parts of the liquid impermeable area of the surface sheet.

(5) The absorbent article according to any of (1) to (3),
wherein a center part of the surface sheet in the lateral direction is the liquid impermeable area,
wherein right and left sides of the liquid impermeable area of the surface sheet are liquid permeable areas, and
wherein the hanging parts of the pair of right and left floating leg gathers are respectively coupled to the liquid permeable areas on the right and left sides of the surface sheet.

(6) The absorbent article according to any of (1) to (3),
wherein the surface sheet that covers the absorber, except for a center part thereof, is formed by folding back the leak preventer on an upper side surface of the absorber from external sides of right and left edge parts of the absorber, and
wherein each of the hanging parts of the pair of right and left floating leg gathers is coupled to a part of the surface sheet, which keeps a distance from the center part of the absorber.

(7) The absorbent article according to any of (1) to (6), further including a support sheet that is present above the surface sheet,
wherein the support sheet is coupled to the hanging parts of the pair of right and left floating leg gathers, and
wherein a second transferring passage for bodily fluids is formed by the hanging parts and the support sheet.

(8) The absorbent article according to (7),
wherein parts where the support sheet is coupled to the hanging parts of the pair of right and left floating leg gathers are included in parts where the surface sheet is coupled to the hanging parts of the pair of right and left floating leg gathers.

(9) The absorbent article according to any of (1) to (8),
wherein the transferring passage for bodily fluids is provided at least in an area of the crotch part.

(10) The absorbent article according to any of (1) to (9),
wherein the transferring passage for bodily fluids is provided at least in an area of the front body.

(11) The absorbent article according to any of (1) to (10),
wherein the transferring passage for bodily fluids is provided at least in an area of the rear body.

(12) The absorbent article according to any of (1) to (8),
wherein the transferring passage for bodily fluids is continuously provided over respective areas of the front body, the crotch part and the rear body.

Effect of the Invention

An absorbent article according to the present invention has a less of a feeling of restraint at the time of wearing and in which the occurrence of hot and stuffy state and rashes is suppressed.

BRIEF DESCRIPTIONS OF THE DRAWINGS

FIG. 1 contains schematic diagrams illustrating the basic structure of an FLG and the forming principles of a "transferring passage for bodily fluids," which is formed by hanging parts of the FLGs and a surface sheet being coupled to each other.

Figure 2:
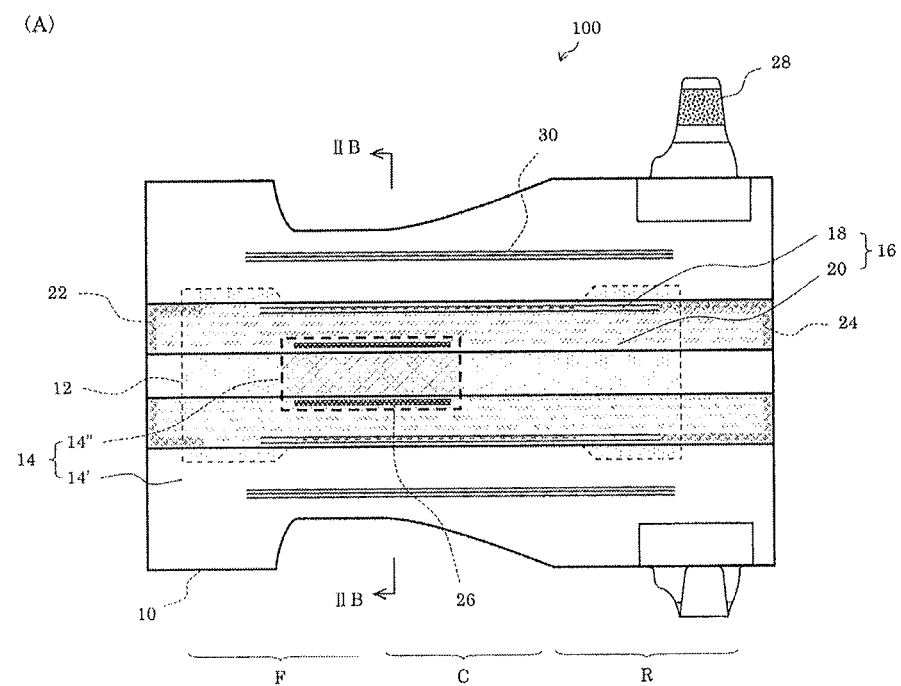
Figure 2:
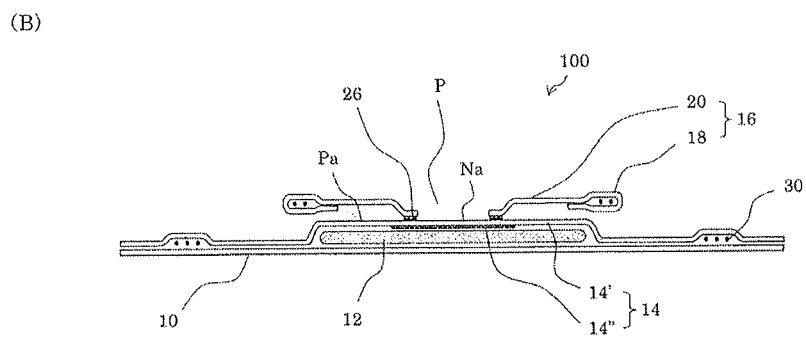

FIG. 2 contains schematic diagrams illustrating an example of the absorbent article according to the present invention.

Figure 3:
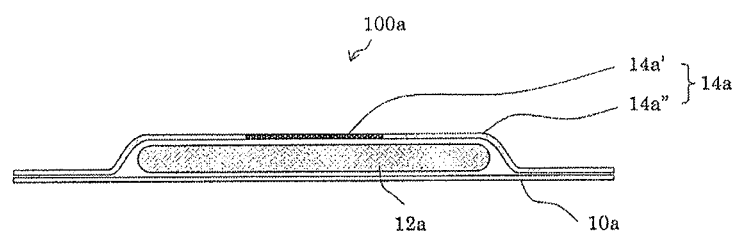
Figure 3:
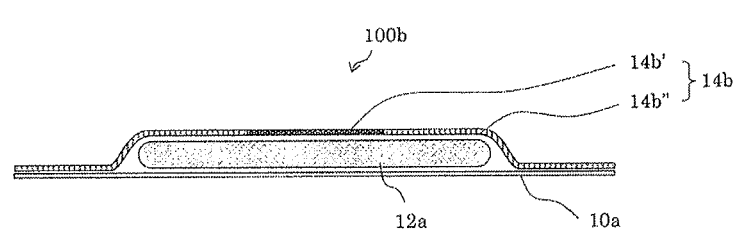
Figure 3:
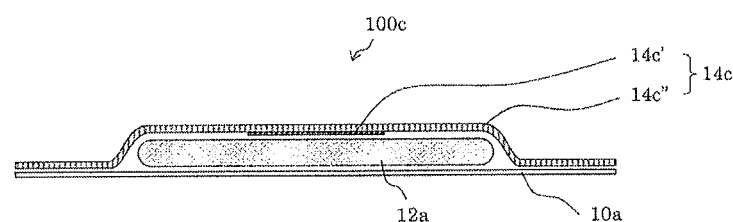
Figure 3:
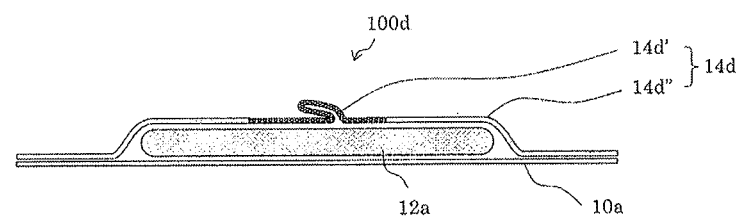
Figure 3:
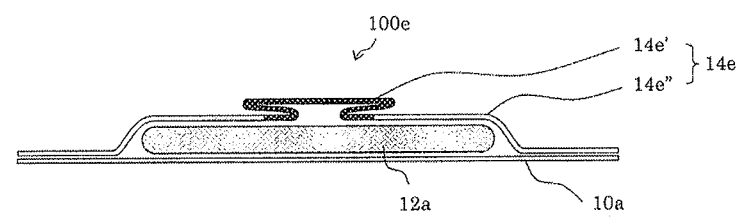
Figure 3:
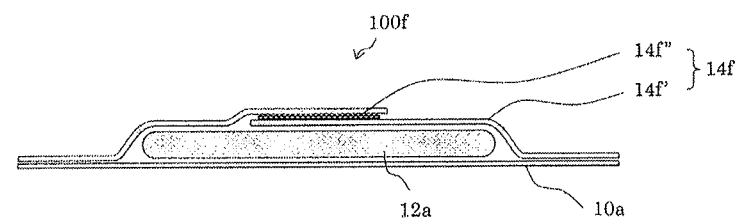

FIG. 3 contains schematic diagrams illustrating the absorbent article according to the present invention with various surface sheets.

Figure 4:
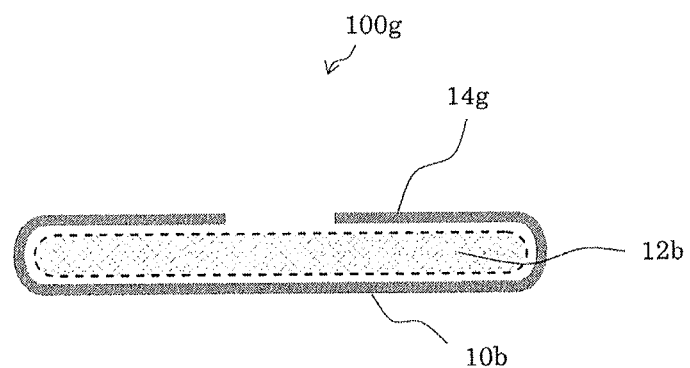
Figure 4:
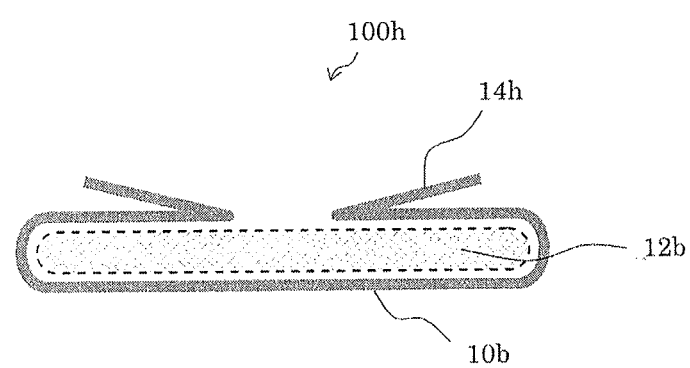
Figure 4:
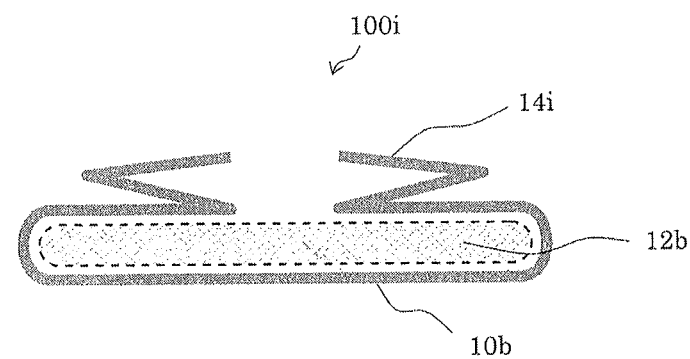

FIG. 4 contains schematic diagrams illustrating the absorbent article according to the present invention with various surface sheets.

Figure 5:
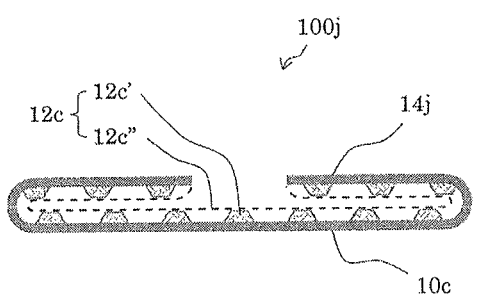
Figure 5:
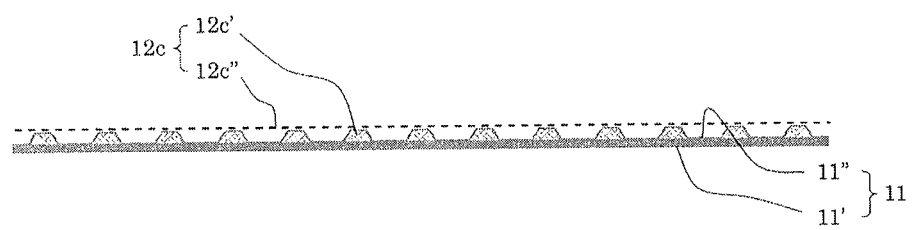
Figure 5:
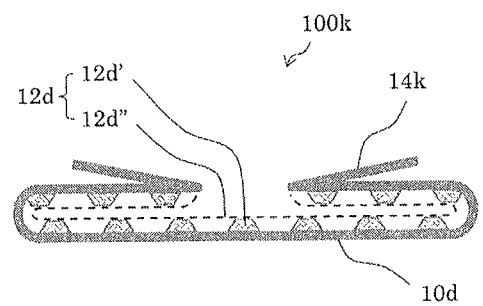
Figure 5:
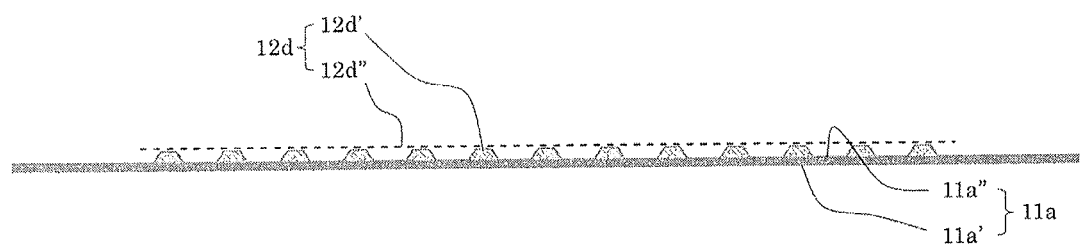

FIG. 5 contains schematic diagrams illustrating the absorbent article according to the present invention with various surface sheets.

Figure 6:
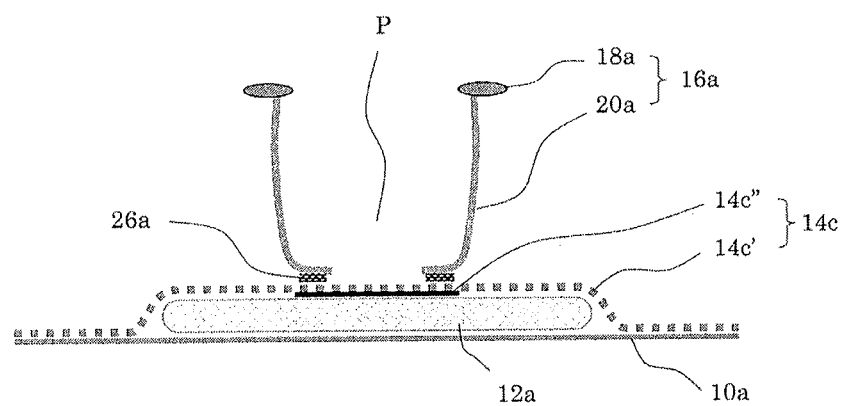
Figure 6:
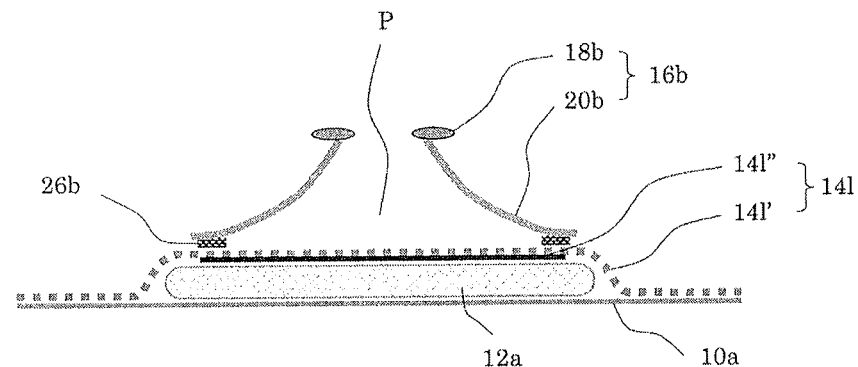

FIG. 6 contains schematic lateral end views illustrating various forms of coupling between hanging parts of FLGs and a surface sheet.

Figure 7:
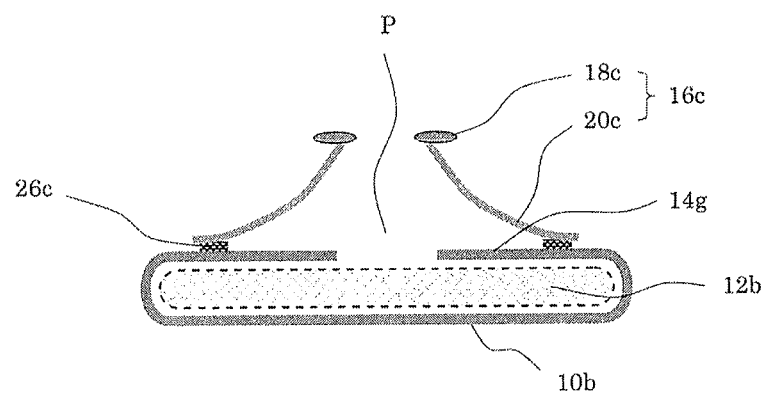
Figure 7:
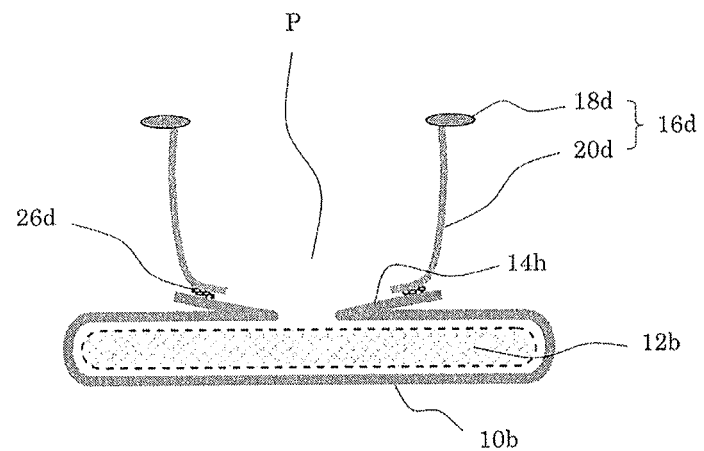

FIG. 7 contains schematic lateral end views illustrating various forms of coupling between hanging parts of FLGs and a surface sheet.

Figure 8:
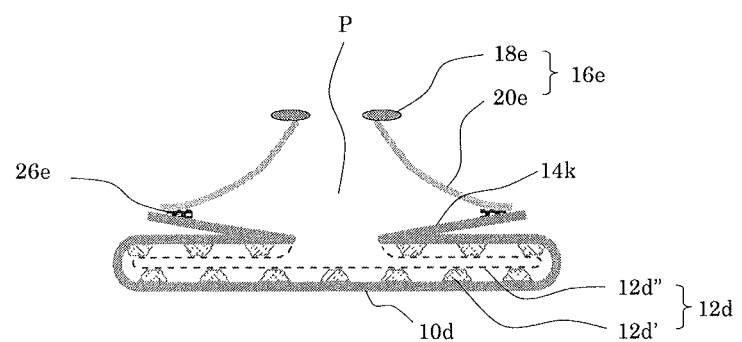
Figure 8:
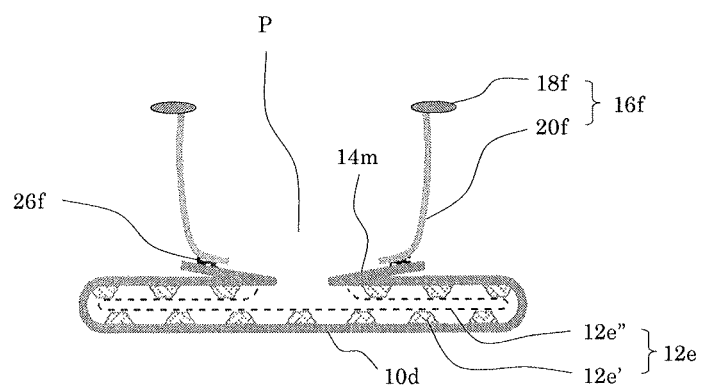

FIG. 8 contains schematic lateral end views illustrating various forms of coupling between hanging parts of FLGs and a surface sheet.

Figure 9:
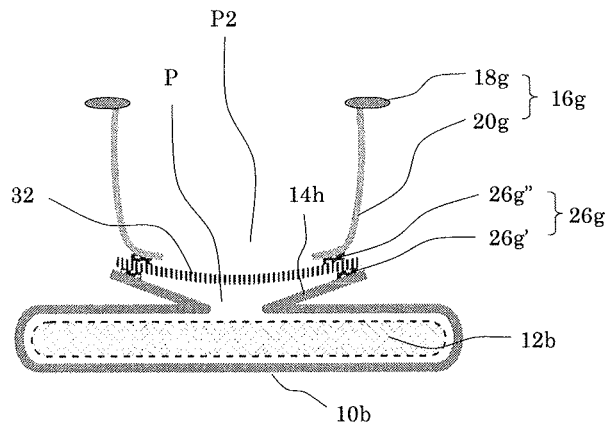
Figure 9:
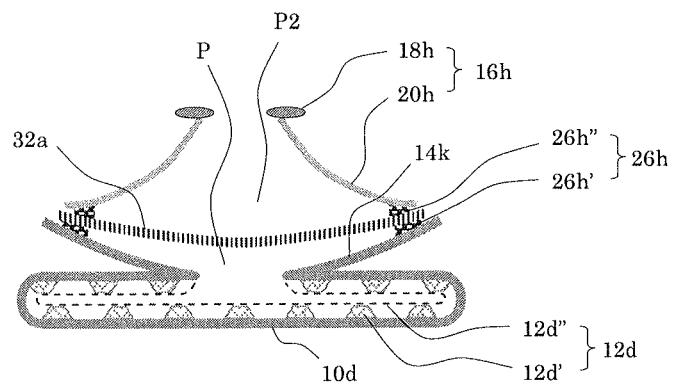
Figure 9:
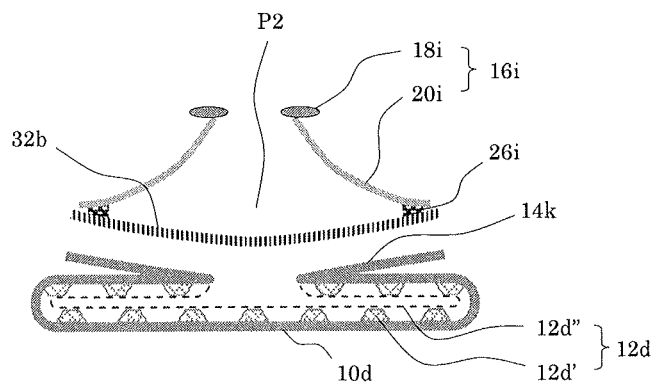

FIG. 9 contains schematic lateral end views illustrating various forms of coupling among hanging parts of FLGs, a surface sheet and a support sheet.

Figure 10:
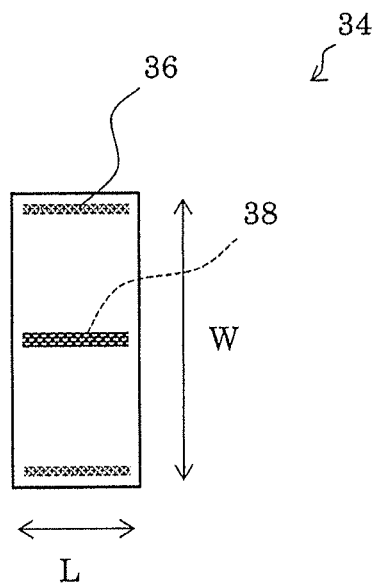
Figure 10:
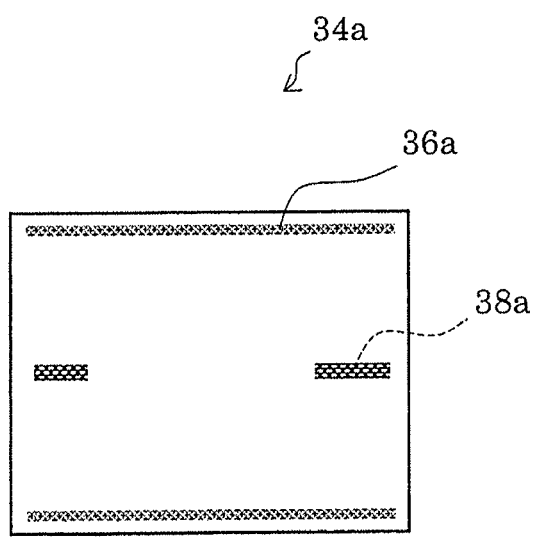
Figure 10:
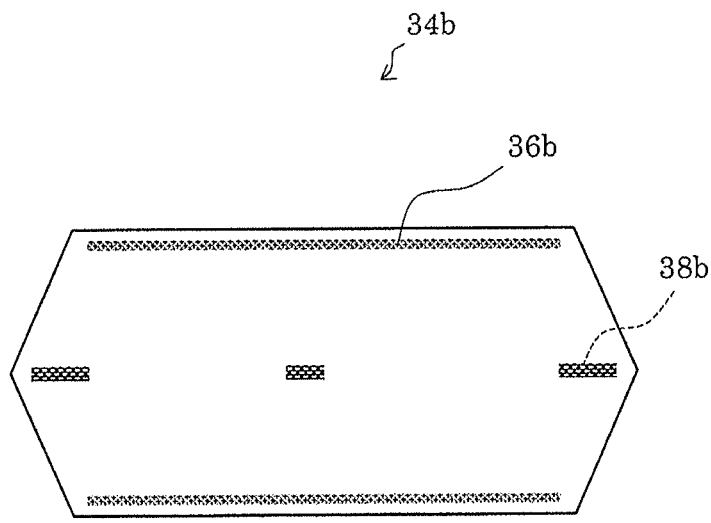
Figure 10:
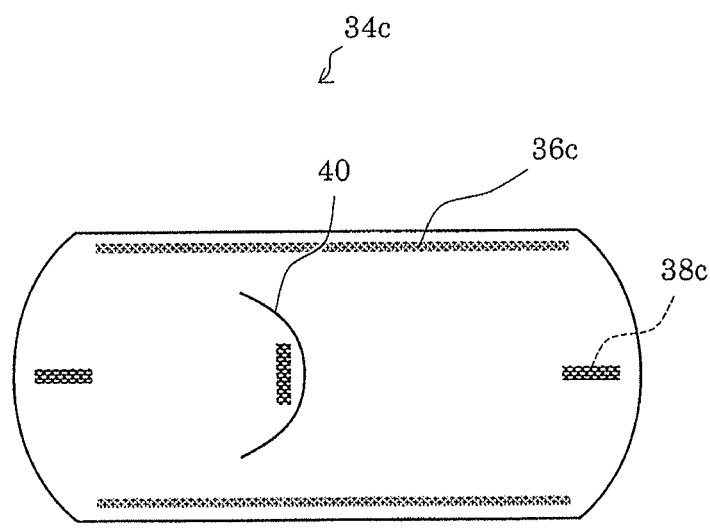
Figure 10:
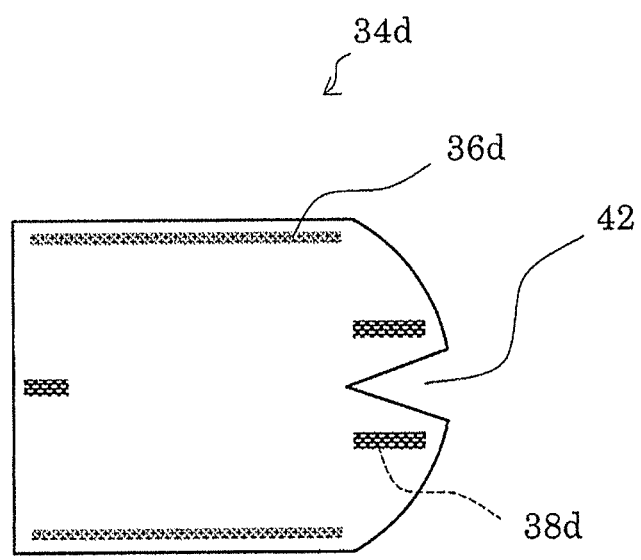

FIG. 10 contains schematic plan views illustrating the configurations of various support sheets.

Figure 11:
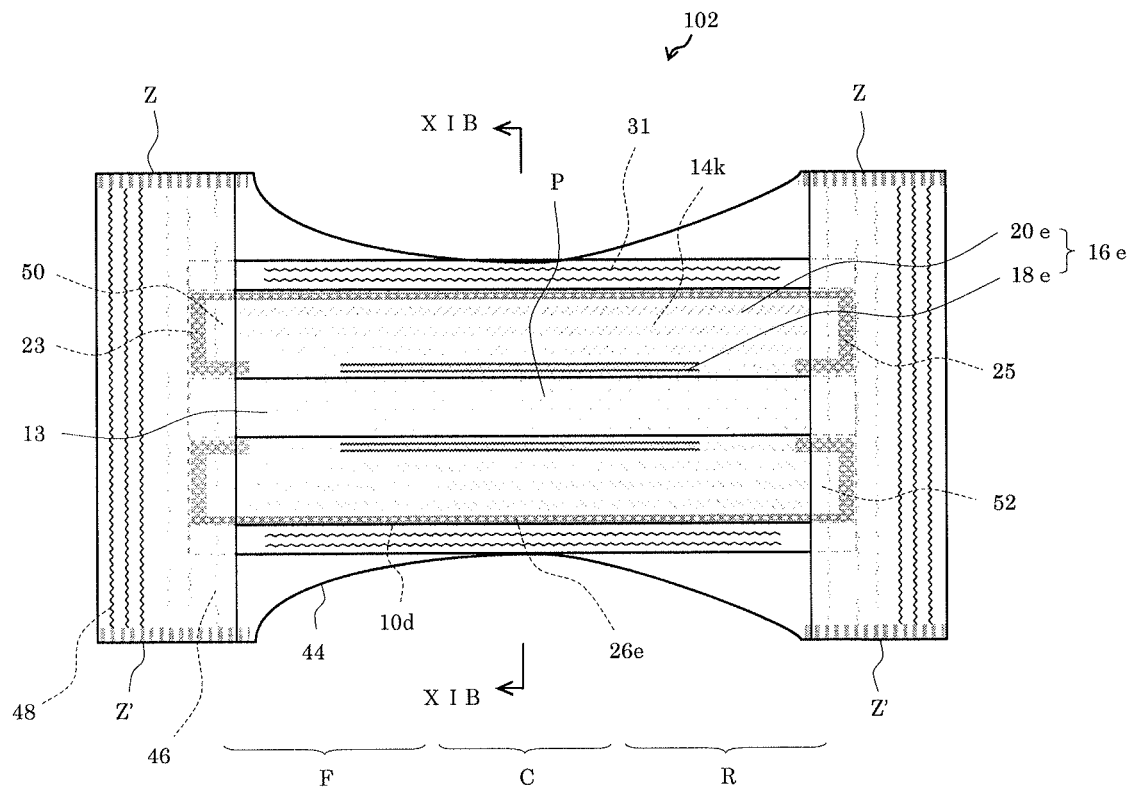
Figure 11:
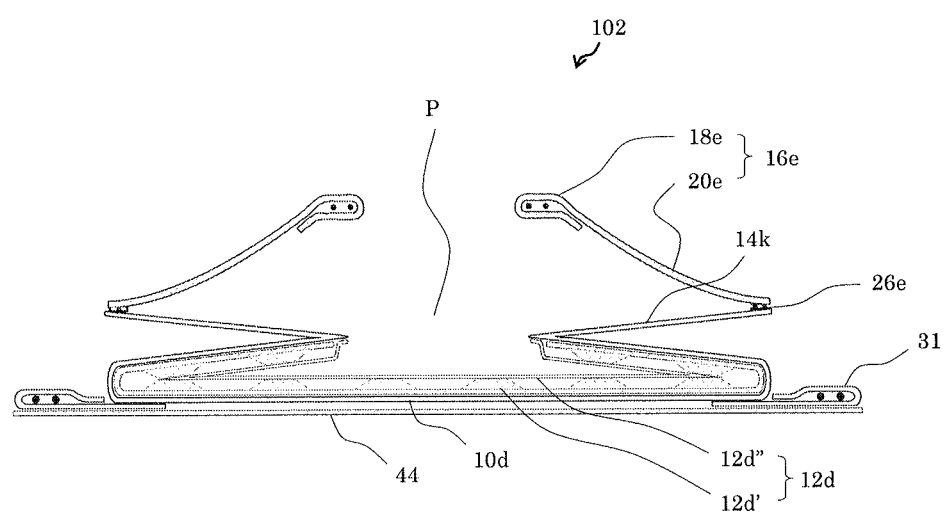

FIG. 11 contains schematic diagrams of an embodiment of the absorbent article according to the present invention.

Figure 12:
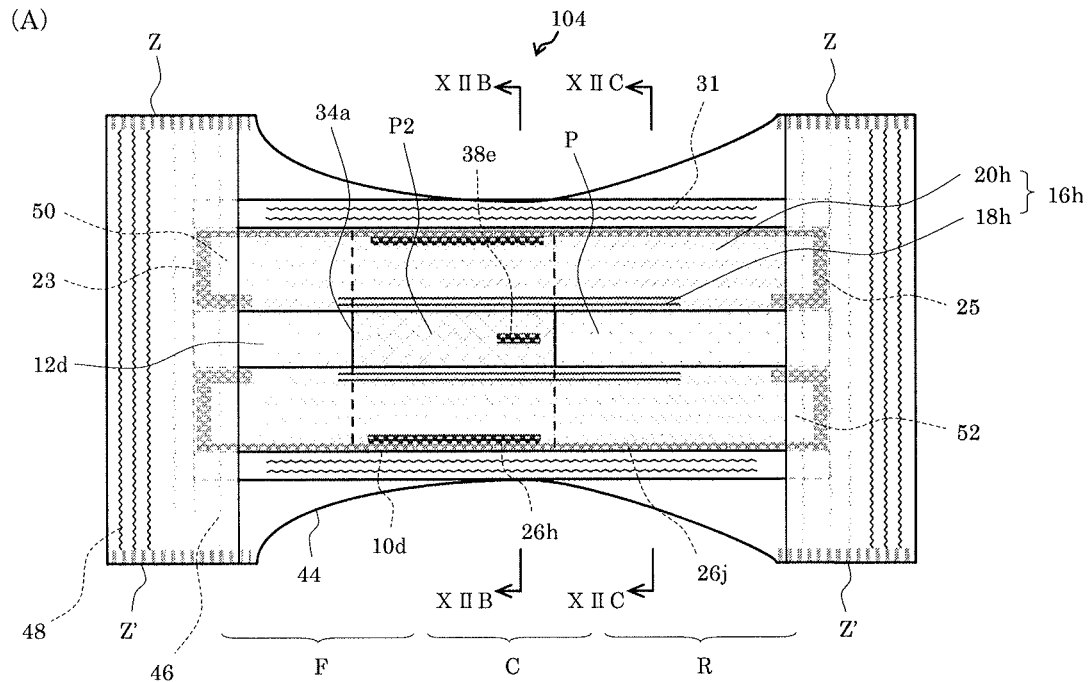
Figure 12:
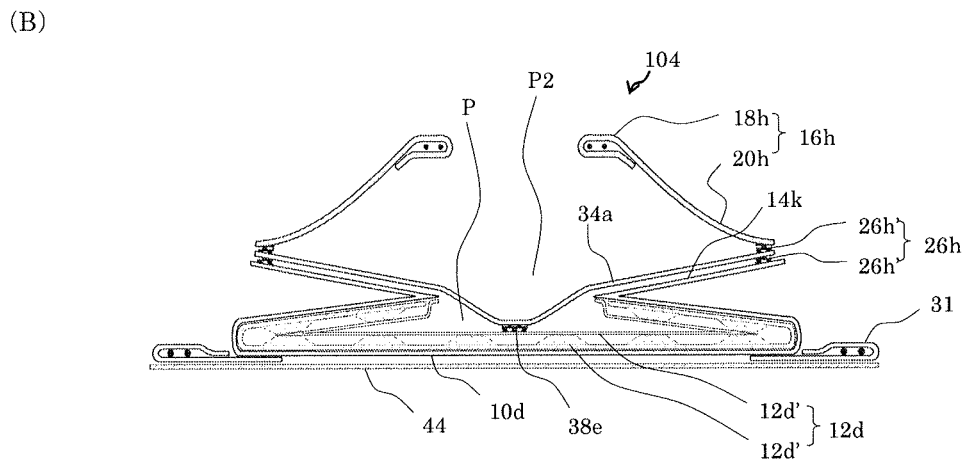
Figure 12:
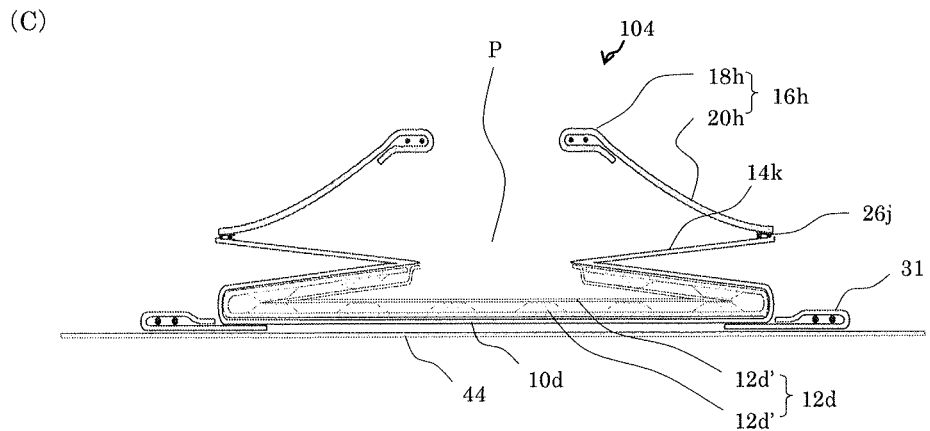

FIG. 12 contains schematic diagrams of another embodiment of the absorbent article according to the present invention.

Figure 13:
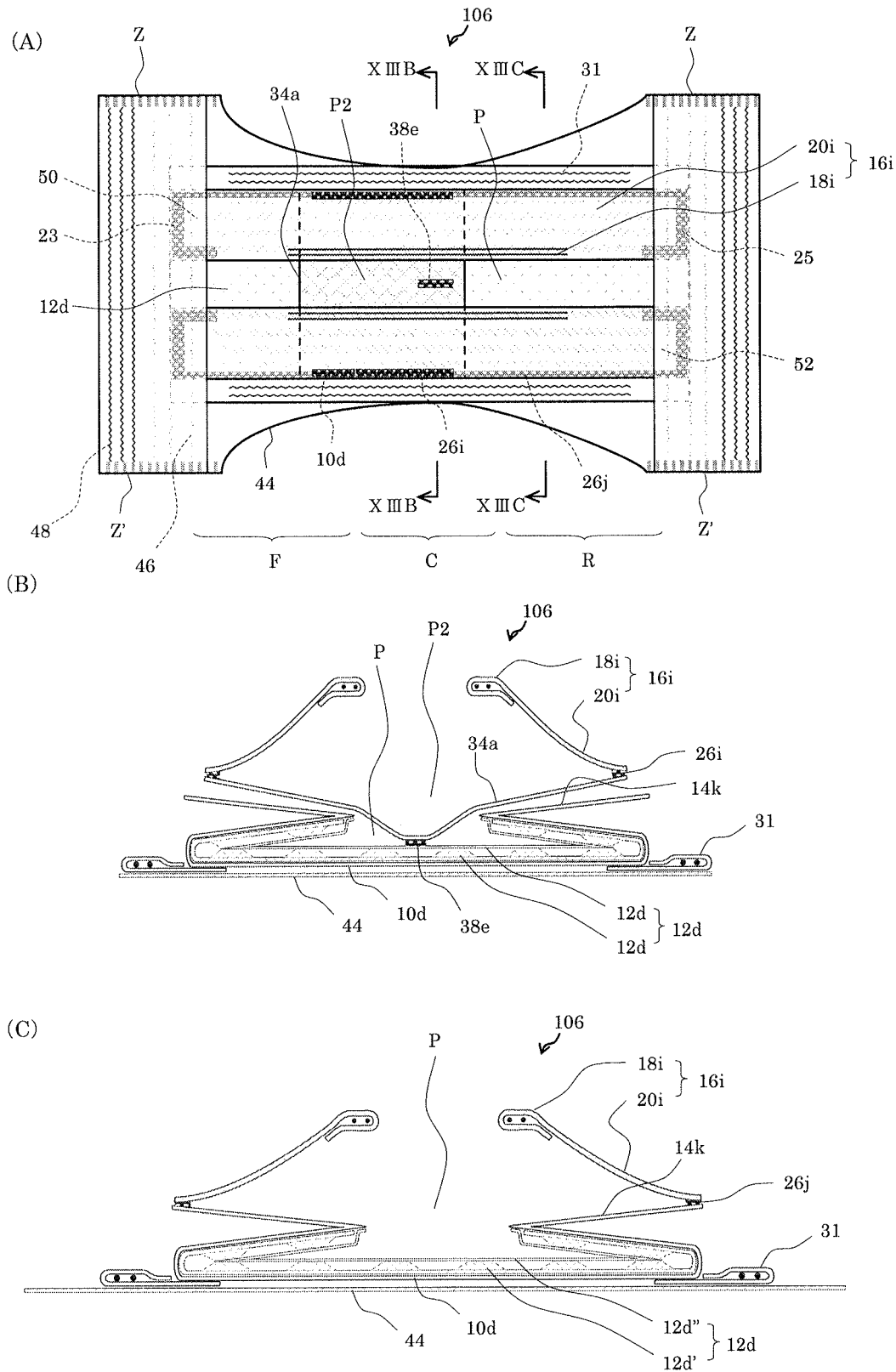

FIG. 13 contains schematic diagrams of a further embodiment of the absorbent article according to the present invention.

EMBODIMENTS OF THE INVENTION

Hereinafter, the absorbent article according to the present invention will be described in detail, based on the preferred embodiments illustrated in the attached drawings. It should be noted that, in the present specification, when the absorbent article according to the present invention is actually worn, a side close to the skin of the wearer will be referred to as the "top" and a side far therefrom will be referred to as the "bottom/under." In addition, when the absorbent article according to the present invention is actually worn, a side corresponding to the front side of the wearer's body will be referred to as the "front" and a side corresponding to the back side thereof will be referred to as the "rear." Moreover, in order to facilitate understanding, in the respective drawings, members that are actually in contact with each other may be illustrated such that they are spaced apart. In the respective plan views among the attached drawings, the front side of the absorbent article or the like is shown to be positioned at the left side of the corresponding drawing.

In addition, in the present specification, an "absorbent article body" collectively refers to a leak preventer, a top sheet that can be provided above the leak preventer and various other members that can be provided to the absorbent article, all of which are constituent members of the absorbent article. In accordance with this, when the absorbent article is a diaper, the absorbent article body will be referred to as a diaper body Moreover, in the present specification, an "absorber surface" refers to a surface of an absorber when it is exposed, or to a surface of a diffusion sheet, acquisition sheet, surface sheet or the like when the absorber is covered with such diffusion sheet, acquisition sheet, surface sheet or the like.

First, the fundamental principles of an FLG used in the absorbent article according to the present invention and of a transferring passage for bodily fluids formed by the FLGs will be described.

FIG. 1 contains schematic diagrams illustrating the basic structure of an FLG and the forming principles of a "transferring passage for bodily fluids," which is formed by hanging parts of the FLGs and a surface sheet being coupled to each other.

FIG. 1(A) is a schematic lateral end view showing the basic structure of an FLG. FIG. 1(A) only shows FLGs, an absorber and a surface sheet in an absorbent article according to the present invention.

FIG. 1(A) shows a state prior to a pair of right and left FLGs 1 being connected to each other. The pair of right and left FLGs 1 include head parts 2 and hanging parts 3 that connect to head parts 2. A front end part and a rear end part of FLG 1 are respectively coupled to the vicinity of a front end part and in the vicinity of a rear end part of the absorbent article body (not shown), and hanging part 3 is configured to hang down from head part 2 toward absorber 4.

As illustrated, FLGs 1 are present in a state (i.e. a floating state) in which a pair of right and left head parts 2 and hanging parts 3 hanging down from head parts 2 are floating from surface sheet 5 located at the surface of absorber 4. In this way, despite the fact that the head parts of the FLGs of the absorbent article according to the present invention are strongly and closely attached to the wearer's body, a feeling of restraint at the time of wearing is reduced.

In addition, above an upper surface of absorber 4, surface sheet 5 is provided which covers at least part of the upper surface and which has a liquid impermeable area at at least part thereof.

In the present invention, each of hanging parts 3 of the pair of right and left FLGs is coupled to surface sheet 5 and transferring passage P for bodily fluids is formed by hanging parts 3 and surface sheet 5.

Examples of the forms of coupling between hanging parts 3 of the FLGs and surface sheet 5 include: (a) a form, such as those shown in FIGS. 1(B) and 1(C), where the pair of right and left FLGs 1 are arranged such that both head parts 2 face outward and both hanging parts 3 face inward (the "inwardly-closed type"); and (b) a form, such as those shown in FIGS. 1(D) and 1(E), where the pair of right and left FLGs 1 are arranged such that both head parts 2 face inward and both hanging parts 3 face outward (the "outwardly-open type"). It should be noted that both FIGS. 1(B) and 1(D) are schematic plan views of the absorbent article according to the present invention, and they show only the FLGs, the absorber and the surface sheet in the absorbent article according to the present invention. In addition, both FIGS. 1(C) and 1(E) are schematic lateral end views of the absorbent article according to the present invention and they show only the FLGs, the absorber and the surface sheet in the absorbent article according to the present invention.

First, the inwardly-closed type form (i.e. the above form (a)) will be described.

In the inwardly-closed type form, as shown in FIGS. 1(B) and 1(C), the pair of right and left hanging parts 3 are arranged, above surface sheet 5, opposite to each other with a gap therebetween, with head parts 2 of FLGs 1 facing outward and hanging parts 3 thereof facing inward.

The vicinities of the lower ends of hanging parts 3 and surface sheet 5 are coupled to each other at coupling parts 6, which are provided in the vicinity of the center in the front-rear direction and which extend in the front-rear direction. This allows transferring passage P for bodily fluids to be formed, which is configured from: both side surfaces formed by the pair of right and left hanging parts 3; and a bottom surface formed by surface sheet 5. The upper part of transferring passage P for bodily fluids is open, since the pair of right and left head parts 2 are spaced apart.

The coupling between the pair of right and left hanging parts 3 and surface sheet 5 is sufficient as long as it is performed at at least part of the FLGs extending in the front-rear direction and transferring passage P for bodily fluids is formed at these coupled parts. The method of coupling the pair of right and left hanging parts 3 and surface sheet 5 is not particularly limited, and they may be coupled using, for example, a hot melt adhesive, a heat sealed bond or the like.

In the inwardly-closed type form, the state of existence of the FLGs is not particularly limited and various states of existence can be employed for the FLGs, as long as: the pair of right and left hanging parts 3 are arranged, above surface sheet 5, opposite to each other with a gap therebetween, with head parts 2 of FLGs 1 facing outward and hanging parts 3 facing inward; the surface sheet is present between the coupling parts of hanging parts 3 of the pair of right and left FLGs 1 and surface sheet 5; and each of hanging parts 3 of the pair of right and left FLGs 1 is coupled to surface sheet 5 so as to form transferring passage P for bodily fluids by hanging parts 3 and surface sheet 5.

More specifically, out of form (1) in which the hanging parts of the FLGs are not connected to the surface sheet and are, thus, present in a floating state (see FIG. 1(A)) and form (2) in which the pair of right and left hanging parts are connected to the surface sheet and thus, a transferring passage for bodily fluids is formed (see FIGS. 1(B) and 1(C)), the absorbent article according to the present invention may have only form (2) or may have both forms (1) and (2). In particular, it is preferable for the absorbent article according to the present invention to have both forms (1) and (2).

In the form shown in FIG. 1(B), the FLGs in form (2) are present at crotch part C and the FLGs in form (1) are present at front body F and rear body R.

Next, the outwardly-open type form (i.e. the above form (b)) will be described.

In the outwardly-open type form, as shown in FIGS. 1(D) and 1(E), the pair of right and left head parts 2 are arranged, above surface sheet 5, opposite to each other with a gap therebetween, with head parts 2 of FLGs 1 facing inward and hanging parts 3 thereof facing outward.

The vicinities of the lower ends of hanging parts 3 and surface sheet 5 are coupled to each other at coupling parts 6', which are provided in the vicinity of the center in the front-rear direction and which extend in the front-rear direction. This allows transferring passage P for bodily fluids to be formed, which is configured from: both side surfaces formed by the pair of right and left hanging parts; and a bottom surface formed by surface sheet 5. The upper part of transferring passage P for bodily fluids is open, since the pair of right and left head parts 2 are spaced apart.

The coupling between the pair of right and left hanging parts 3 and surface sheet 5 is sufficient as long as it is performed at at least part of the FLGs extending in the front-rear direction and transferring passage P for bodily fluids is formed at these coupled parts. The method of coupling the pair of right and left hanging parts 3 and surface sheet 5 is not particularly limited, and they may be coupled using, for example, a hot melt adhesive, a heat sealed bond or the like.

In the outwardly-open type form, the state of existence of the FLGs is not particularly limited and various states of existence can be employed for the FLGs, as long as: the pair of right and left head parts 2 are arranged, above surface sheet 5, opposite to each other with a gap therebetween, with head parts 2 of FLGs 1 facing inward and hanging parts 3 thereof facing outward; the surface sheet is present between the coupling parts of hanging parts 3 of the pair of right and left FLGs 1 and surface sheet 5; and each of hanging parts 3 of the pair of right and left FLGs 1 is coupled to surface sheet 5 so as to form transferring passage P for bodily fluids by hanging parts 3 and surface sheet 5.

More specifically, out of form (1) in which the hanging parts of the FLGs are not connected to the surface sheet and are, thus, present in a floating state (see FIG. 1(A)) and form (3) in which the pair of right and left hanging parts are connected to the surface sheet so as to form a transferring passage for bodily fluids (see FIGS. 1(D) and 1(E)), the absorbent article according to the present invention may have only form (3) or may have both forms (1) and (3). In particular, it is preferable for the absorbent article according to the present invention to have both forms (1) and (3).

In the form shown in FIG. 1(D), the FLGs in form (3) are present at crotch part C and the FLGs in form (1) are present at front body F and rear body R.

In the present invention, at which position in the front-rear direction this state of existence of the FLGs should be provided and how the combination should be made when two types of forms are to be combined are the key points in designing the absorbent article.

When the transferring passage for bodily fluids is provided at least in the area of the crotch part, the transferring passage for bodily fluids is located directly below the excretory organ for urine (i.e. the meatus urethra), and thus, the reception of urine is facilitated.

When the transferring passage for bodily fluids is provided at least in the area of the front body, it can be used as a passage for transferring the urine from the front to the rear.

When the transferring passage for bodily fluids is provided at least in the area of the rear body, the transferring passage for bodily fluids is located at a location close to the excretory organ for feces (i.e. the anus), and thus, the reception of feces is facilitated.

When the transferring passage for bodily fluids is provided in a continuous manner over the respective areas of the front body, the crotch part and the rear body, the above-described advantages can be simultaneously obtained.

The above form (a) (i.e. the inwardly-closed type form) and the above form (b) (i.e. the outwardly-open type form) differ in the cross-sectional shape of transferring passage P for bodily fluids.

More specifically, when, for example, the lengths between the part of the hanging part connecting to the head part and the part of the hanging part coupling to the surface sheet are the same, transferring passage P for bodily fluids in the inwardly-closed type form is a narrow and deep passage, with the width of the bottom surface in the lateral direction being narrow and both side surfaces being high. In contrast, transferring passage P for bodily fluids in the outwardly-open type form is a wide and shallow passage, with the width of the bottom surface in the lateral direction being wide and both side surfaces being low.

FIG. 2 contains schematic diagrams illustrating an example of the absorbent article according to the present invention. FIG. 2(A) is a developed plan view and FIG. 2(B) is a lateral end view along line IIB-IIB in FIG. 2(A). FIG. 2 schematically shows the state in which stress is applied to the absorbent article such that it is pulled in the front-rear direction and the lateral direction to be developed into a substantially planar form.

Absorbent article 100 of the present invention shown in FIG. 2 is configured as a tape-type diaper and is basically provided with: leak preventer 10 in sheet form; absorber 12 capable of absorbing a bodily fluid, wherein at least a layer thereof is arranged above leak preventer 10; surface sheet 14 that covers the entire upper surface of absorber 12 and that has liquid impermeable area Na at a part thereof; and a pair of right and left FLGs 16 that are arranged, above absorber 12, from a front end part in the length direction of the absorbent article body to a rear end part thereof via front body F, crotch part C and rear body R.

Materials that are generally used as a back sheet can be used for the materials of leak preventer 10. In particular, a resin film made of, for example, PE, PP, PET, EVA or the like and a bodily fluid impermeable sheet such as a foam sheet made of the resin described above can be used. For the bodily fluid impermeable sheet, a sheet having air permeability, such as an air permeable sheet or the like may be preferably used.

In addition, when the above-described resin film is used, a multilayered sheet of such film and a non-woven fabric may be used in order to improve the texture and appearance. In this case, a spunbond (SB) or thermalbond non-woven fabric (for example, an air-through type) having a relatively low basis weight or the like may preferably be used as the non-woven fabric.

Moreover, a multilayered sheet of such resin film and an absorber in sheet form, which will be described below, may also be used.

Further, a high water-resistance non-woven fabric may also be used. Examples of such high water-resistant non-woven fabric include an SMS non-woven fabric having a degree of water resistance of 100 mm H$_2$O or more and an SMS non-woven fabric in which pores in a non-woven web are filled with microfibrillated cellulose (MFC) or wax so as to provide such fabric with water resistance. In this case, a high water-resistant non-woven fabric may be used alone or may also be used as a multilayered sheet of the film and such high water-resistant non-woven fabric.

Leak preventer 10 may be configured from a plurality of members.

Leak preventer 10 is in sheet form; however, it is not particularly limited in terms of shape as long as it accommodates absorber 12, or the like, above itself and is capable of being arranged with FLGs 16 thereon.

Absorber 12 used in the present invention is not particularly limited, as long as it is capable of absorbing bodily fluid, and any absorber used in publicly known conventional absorbent articles may be used. Examples such as: pulverized wood pulp; an absorber in which pulverized wood pulp and flake shape or powdery SAP are mixed and shaped into a mat; a sheet-like absorber formed into a thin sheet and having SAP as a primary component, or the like, may be used. These absorbers keep the shape thereof and at the same time prevent the generation or droppage of fine powder from pulp and SAP. Thus, in general, the absorbers are covered with a core wrapping material made of tissue paper, a non-woven fabric, a perforated film, or the like. In the present specification, when a core wrapping material is used, such core wrapping material is also inclusively referred to as an "absorber."

An absorber in sheet form excels in morphological stability and capability of SAP fall prevention, etc.

Among various types of absorber in sheet form, a super absorbent sheet containing 50 weight % or more, preferably 60 weight % or more, or more preferably 70 weight % or more of SAP is preferred. In addition, from the perspective of stability, etc. of the super absorbent sheet, the content of SAP therein is preferably 95 weight % or less.

The super absorbent sheet is an extremely-thin absorber in sheet form having SAP as a primary component. Since the content of SAP is extremely high, the thickness of the super absorbent sheet is extremely low. The thickness of the super absorbent sheet is preferably 1.5 mm or less and more preferably 1 mm or less.

The super absorbent sheet is not particularly limited in terms of its configuration and production method, as long as it is an extremely-thin absorber in sheet form having SAP as a primary component.

For example, there is a super absorbent sheet obtained by an Air-Laid process. In the Air-Laid process, crushed wooden pulp and SAP are mixed and a binder is added to shape the mixture into a sheet form and then a super absorbent sheet is obtained. As examples of a super absorbent sheet obtained through this process, NOVATHIN (US registered trademark) manufactured by Rayonier Inc. in the US, B-SAP manufactured by Oji Kinocloth Co., Ltd., or the like, are known.

Another example of the super absorbent sheet includes a super absorbent sheet obtained through a process involving coating a bodily fluid permeable sheet such as a non-woven fabric with SAP-dispersed slurry. Here, the SAP-dispersed slurry is preferably prepared by dispersing SAP and microfibrillated cellulose (MFC) in a mixed solvent of water and ethanol. As an example of the super absorbent sheet obtained through this process, MegaThin (trademark) manufactured by Japan Absorber Technology Institute is known.

Other examples of the super absorbent sheet include: a super absorbent sheet obtained through a process involving having a raised non-woven fabric carry a large amount of SAP and fixing the SAP with a hot melt binder, an emulsion binder, a water-soluble fiber, or the like; a super absorbent sheet obtained through a process involving mixing fibrous SAP with a PET (polyethylene terephthalate) fiber and forming the mixture into a web; and an SAP sheet obtained by providing tissues above and below an SAP layer.

At least one layer of absorber 12 is arranged above leak preventer 10. Namely, absorber 12 may be comprised of one layer or two or more layers (multilayer).

In addition, absorber 12 may be arranged in a folded condition.

Absorbent article 100 according to the present invention is provided with surface sheet 14 that covers the entire upper surface of absorber 12 and that has liquid impermeable area Na at a part thereof.

Surface sheet 14 is configured by apertured film 14' and sealing film 14" that couples to the underside of aperture film 14' from front body F to crotch part C at the center part in the lateral direction. Apertured film 14' has a plurality of apertures and is a film which allows a liquid to permeate through such apertures. For example, an apertured film made of PE and having liquid permeable funnel-shaped apertures over the entire surface thereof (manufactured by, for example, TREDEGAR Corporation) may be used.

Sealing film 14" is a liquid impermeable film and is configured using, for example, PE, PET, synthetic rubber or polyurethane.

Sealing film 14" of surface sheet 14 is coupled to the underside of apertured film 14', and the part where sealing film 14" is present is liquid impermeable area Na and the part where sealing film 14" is not present is liquid permeable area Pa.

In the present invention, the surface sheet is sufficient as long as it has a liquid impermeable area at least part thereof. More specifically, the surface sheet may have a liquid impermeable area at only a part thereof or may have a liquid impermeable area at the entirety thereof.

Surface sheet 14 covers the entire upper surface of absorber 12 and also covers the entire surfaces of the right and left ends, the front end and the rear end of absorber 12.

In the present invention, the surface sheet is sufficient as long as it covers at least a part of the upper surface of the absorber. More specifically, the surface sheet may cover only a part of the upper surface of the absorber or it may cover the entire upper surface of the absorber. In addition, the surface sheet may cover not only the upper surface of the absorber but also a part of or the entirety of the upper surface of the leak preventer.

The pair of right and left FLGs 16 are arranged, above absorber 12, from a front end part in the length direction of the absorbent article body to a rear end part thereof via front body F, crotch part C and rear body R. The FLGs may be provided by being coupled to the leak preventer, may be provided by being coupled to a surface sheet or other members provided on the leak preventer, or may be provided by being coupled to a plurality of members.

FLG 16 includes head part 18 which is configured by having a stretchable member (for example, the two parallel polyurethane filaments depicted in wavy lines in FIG. 2) and hanging part 20 which continues to head part 18. FLG 16 is configured such that a front end part and a rear end part (i.e. parts where the polyurethane filaments are not present in FIG. 2) of head part 18 are respectively coupled to the vicinity of a front end part and the vicinity of a rear end part of the absorbent article body (front end coupling part 22 and rear end coupling part 24 are shown in FIG. 2) and such that hanging part 20 hangs down from head part 18 toward absorber 12. The coupling method is not particularly limited and, for example, the coupling method may be achieved by means of an adhesive.

Hanging part 20 hangs down from head part 18 in curtain form and it does not stand up due to being coupled to, fixed to and supported by the surface of the absorber (or the top sheet covering the absorber) as in conventional ILGs. Basically, hanging part 20 floats from surface sheet 14 corresponding to the surface of absorber 12. Since such new FLG 16 has a floating configuration as described above, it will be herein referred to as a floating leg gather (FLG). Such floating configuration may be realized by making, for example, the length between front end coupling part 22 and rear end coupling part 24 in FLG 16 shorter than the length between front end coupling part 22 and rear end coupling part 24 in leak preventer 10.

Each of the parts of hanging parts 20 of the pair of right and left FLGs 16 is coupled to surface sheet 14 so that transferring passage P for bodily fluids is formed.

More specifically, in each of the pair of right and left FLGs 16, head part 18 is arranged to face outward and hanging part 20 is arranged to face inward. Hanging parts 20 of the pair of right and left FLGs 16 are arranged opposite to each other with a gap therebetween. Surface sheet 14 is present between coupling parts 26 of hanging parts 20 of the pair of right and left FLGs 16 with surface sheet 14.

In addition, the center part of surface sheet 14 in the lateral direction is liquid impermeable area Na and the right and left sides of liquid impermeable area Na of surface sheet 14 are liquid permeable areas Pa. Each of hanging parts 20 of the pair of right and left FLGs 16 is coupled to the vicinity of the corresponding right or left edge part of liquid impermeable area Na of surface sheet 14 at coupling part 26 that extends in the front-rear direction.

Except for the part coupling to surface sheet 14, FLG 16 is not fixed to surface sheet 14 corresponding to the surface of absorber 12 from a front end part thereof to a rear end part thereof and thus, is spaced apart from surface sheet 14 corresponding to the surface of absorber 12. Namely, FLG 16 is present in a floating state.

In absorbent article 100, since FLGs 16 employ the above-described configuration, in the area from front body F to crotch part C, transferring passage P for bodily fluids is formed by the pair of right and left hanging parts 20 and surface sheet 14, with the respective inner surfaces thereof configuring the right and left side surfaces and the bottom surface. The upper part of transferring passage P for bodily fluids is open, since the pair of right and left head parts 18 are spaced apart.

At the time of wearing, the form shown in FIG. 1(A) is assumed, except for the parts of the pair of right and left FLGs 16 which are coupling to surface sheet 14.

At the time of wearing, head parts 18 of FLGs 16 make contact with the wearer's skin.

The present invention is not limited to the above-described configuration and, for example, various publicly-known conventional members may be provided.

In addition to the members described above, absorbent article 100 is provided with various other members described below.

Detachable members 28 are provided on both the right and left sides of leak preventer 10 in the vicinity of the rear end thereof. On the under surface of leak preventer 10 in the vicinity of the front end thereof, detachable members (not shown) are provided such that they can be detached from detachable members 28. These detachable members may be configured by, for example, various hook-and-loop fasteners. In particular, as for detachable members 28 provided on both the right and left sides of leak preventer 10 in the vicinity of the rear end thereof, Velcro tapes (male) may be used. As for the detachable members provided on the under surface of leak preventer 10 in the vicinity of the front end, tape landing zones, known as TLZs (female), may be used.

In addition, absorbent article 100 is provided with two types of leg gathers. In particular, in addition to the above-described FLGs 16, OLGs 30 are provided, which are present in the side edge parts of the absorbent article body. OLG 30 is formed by three parallel polyurethane filaments (stretchable members) being arranged between leak preventer 10 and surface sheet 14.

In absorbent article 100 according to the present invention, since FLGs 16 are present in a floating state, a feeling of restraint at the time of wearing is reduced.

In addition, the occurrence of hot and stuffy state and rashes is suppressed.

In absorbent article 100 according to the present invention, contact between the excreted urine and/or feces and the wearer's skin is significantly suppressed as compared to conventional diapers, since the presence of head parts 18 and hanging parts 20 of FLGs 16 serves as a physical obstacle to the wearer's skin making contact with the surface of the absorber.

Accordingly, in conventional absorbent articles, rewetting, dryness, reduction of friction against the skin or the like were important considerations for the top sheet that makes contact with the wearer's skin; however, with the absorbent article according to the present invention, such points do not need to be considered.

Thus, the surface sheet used in the absorbent article according to the present invention may be of a hydrophilic material (for example, a cellulosic material) that excels in diffusion and/or permeability of water or of a material that excels only in the liquid distribution function as in the apertured film made of PE.

A significant suppression in raw material costs is also possible, since the need is eliminated for using an acquisition layer (AQL) which is a temporary reservoir layer for a bodily fluid, a diffusion layer (transfer layer) for promoting diffusion of a bodily fluid or the like, which are arranged in conventional absorbent articles to enhance the function of the top sheet.

Next, the surface sheet used in the absorbent article according to the present invention will be described.

FIGS. 3 to 5 all contain schematic diagrams illustrating the absorbent article according to the present invention with various surface sheets. In FIGS. 3 to 5, members other than the leak preventer, the absorber and the surface sheet are omitted.

FIG. 3 contains schematic lateral end views of the absorbent article according to the present invention with various surface sheets. All of the surface sheets shown in FIG. 3 have the center part thereof in the lateral direction as a liquid impermeable area and the right and left sides of the liquid impermeable area of the surface sheet as liquid permeable areas. Preferably, this type of surface sheet is used in combination with a so-called thin absorber, which is made of the conventional SAP/pulp mixed layer, with an SAP content of less than 50%.

Absorbent article 100a shown in FIG. 3(A) has surface sheet 14a configured by liquid impermeable sheet 14a' which is present in the center part in the lateral direction and liquid permeable sheets 14a" which are present on the right and left sides of liquid impermeable sheet 14a'.

Liquid impermeable sheet 14a' and liquid permeable sheets 14a" are integrated and, for example, a hydrophobic and water-resistant non-woven fabric (for example, a PP SMS non-woven fabric having a basis weight of approximately 15 g/m² (manufactured by, for example, AVGOL Nonwoven Industries)) may be used, in which the center part thereof is left intact by utilizing the water resistance thereof and the right and left sides are provided with liquid permeability through surfactant treatment. Materials configuring the non-woven fabric are not particularly limited and examples of such non-woven fabric include a PE non-woven fabric and a PET non-woven fabric. In addition, for example, a hydrophilic non-woven fabric may be used, in which the center part thereof is made liquid impermeable through water repellent treatment and the right and left sides thereof are left intact by utilizing the hydrophilicity thereof.

Absorbent article 100b shown in FIG. 3(B) has surface sheet 14b configured by liquid impermeable sheet 14b' which is present in the center part in the lateral direction and liquid permeable sheets 14b" which are present on the right and left sides of liquid impermeable sheet 14b'.

Surface sheet 14b is configured by a liquid impermeable film, and apertures are provided in the parts of liquid permeable sheet 14b" so that liquid permeability is obtained. The liquid impermeable film is not particularly limited and, for example, films made of PE, PET, synthetic rubber or polyurethane may be used. The surface of the liquid impermeable film may be smooth or have irregularities.

As a preferred embodiment of surface sheet 14b, for example, in the parts of liquid permeable sheet 14b" of the liquid impermeable film which has irregularities on the surface thereof, the film in the vicinities of the tops of the irregularities may be removed to provide funnel-shaped apertures so as to obtain liquid permeability.

Absorbent article 100c shown in FIG. 3(C) has surface sheet 14c configured by apertured film 14c' and sealing films 14c", which are present in the center part in the lateral direction on the underside of aperture film 14c'. Apertured film 14c' has a plurality of apertures and is a film which allows a liquid to permeate through such apertures. For example, an apertured film made of PE and having liquid permeable funnel-shaped apertures over the entire surface thereof (manufactured by, for example, TREDEGAR Corporation) may be used. Sealing film 14c" is a liquid impermeable film and configured using, for example, PE, PET, synthetic rubber or polyurethane.

Absorbent article 100d shown in FIG. 3(D) has surface sheet 14d configured by liquid impermeable sheet 14d' which is present in the center part in the lateral direction and liquid permeable sheets 14d" which are present on the right and left sides of liquid impermeable sheet 14d'.

Absorbent article 100d is basically similar to absorbent article 100a shown in FIG. 3(A); however, the shape of surface sheet 14d (in particular, the shape of the center part in the lateral direction) is different. Specifically, a part of liquid impermeable sheet 14d' of surface sheet 14d is folded on the left side and thus, the length in the lateral direction is increased in the case of extension.

In this embodiment, the area of the base of the transferring passage for bodily fluids formed by the hanging parts (not shown) of the FLGs and surface sheet 14d is increased. Accordingly, the cross-sectional area of the transferring passage for bodily fluids is increased and the capacity to envelop the bodily fluids and to temporarily store them can also be increased.

Absorbent article 100e shown in FIG. 3(E) has surface sheet 14e configured by liquid impermeable sheet 14e' which is present in the center part in the lateral direction and liquid permeable sheets 14e" which are present on the right and left sides of liquid impermeable sheet 14e'.

Absorbent article 100e is basically similar to absorbent article 100a shown in FIG. 3(A); however, the shape of surface sheet 14e (in particular, the shape at the center part in the lateral direction) is different. Specifically, parts of liquid impermeable sheet 14e' of surface sheet 14e are folded on both the right and left sides and thus, the position of the bottom surface of the transferring passage for bodily fluids moves vertically.

In this embodiment, the bottom surface of the transferring passage for bodily fluids formed by the hanging parts (not shown) of the FLGs and surface sheet 14d tends to float upward. Accordingly, as compared to absorbent articles 100a to 100d, it is easier to keep the spaced state between the skin and the absorber in absorbent article 100e and thus, a feeling of restraint at the time of wearing is even further reduced.

Absorbent article 100f shown in FIG. 3(F) has surface sheet 14f configured by two liquid permeable sheets 14f,' which cover absorber 12a from the right and left sides to the center part, and adhesion part 14f'" that couples the two sheets at the overlapping parts thereof.

Liquid permeable sheet 14f' is not particularly limited and, for example, a liquid permeable non-woven fabric may be used. An example of the liquid permeable non-woven fabric includes a non-woven fabric treated with hydrophilization. An example of the non-woven fabric treated with hydrophilization includes a PE/PP SB non-woven fabric.

Adhesion part 14f may be formed by a sealing material, a water-resistant adhesive (for example, a hot melt adhesive) or the like, and is liquid impermeable.

FIG. 4 contains schematic lateral end views of the absorbent article according to the present invention with various surface sheets. All of the surface sheets shown in FIG. 4 have a leak preventer (back sheet) being folded from external sides of the right and left edge parts of an absorber onto the upper side surface of the absorber so as to cover the absorber, except for the center part thereof. The center part of the surface sheet in the lateral direction is the liquid permeable area and the right and left sides of the liquid permeable area of the surface sheet are the liquid impermeable areas. Preferably, this type of surface sheet is used in combination with a so-called super-thin absorber, which is made of the conventional SAP/pulp mixed layer, with an SAP content of more than 50%. In an absorber, when the SAP content increases, the absorption capacity also increases; however, the absorption speed decreases and blockage is likely to occur. The excreted bodily fluids need to be distributed over the entire absorber as soon as possible, and thus, since the distribution of the bodily fluids in this type of surface sheet is fast, it is preferably used in combination with the super-thin absorber.

Absorbent article 100g shown in FIG. 4(A) has leak preventer 10b covering absorber 12b, except for the center part thereof, from external sides of the right and left edge parts of absorber 12b, with the upper side surface of absorber 12b serving as surface sheet 14g.

Leak preventer 10b is not particularly limited, as long as it has a leak prevention property, and it may be a single film or a non-woven fabric artifact. In particular, a composite sheet of a PE/PP SB non-woven fabric (having, for example, a basis weight of approximately 12 g/m$^2$ (manufactured by, for example, Chisso Corporation)) and an air permeable PE film (having, for example, a basis weight of approximately 17 g/m$^2$ (manufactured by, for example, Tokuyama Corporation)) may preferably be used.

In one of the preferred embodiments, the gap between the edge parts of the right and left sides of surface sheet 14g is preferably approximately 50 mm.

In this case, the arrangement of the composite sheet is not particularly limited; however, it is preferable to arrange the PE film side on the inner side that makes contact with absorber 12b (i.e. on the underside at the part where surface sheet 14g is present) and to arrange the SB non-woven fabric on the upper side that may make contact with the wearer's skin (i e on the upper side at the part where surface sheet 14g is present).

Absorbent article 100h shown in FIG. 4(B) has leak preventer 10b covering the upper side surface of absorber 12b from external sides of the right and left edge parts of absorber 12b and further being folded back outward. Such part of leak preventer 10b that covers the upper side surface of absorber 12b and such folded-back part thereof configure surface sheet 14h, and absorber 12b is covered, except for the center part thereof.

Accordingly, the cross-sectional area of the transferring passage for bodily fluids, which is formed through the coupling between this surface sheet and the hanging parts, is increased, and thus, the capacity to receive the bodily fluids and to temporarily store them can also be increased.

Absorbent article 100i shown in FIG. 4(C) has leak preventer 10b covering the upper side surface of absorber 12b from external sides of the right and left edge parts of absorber 12b and further being folded back outward and then even further being folded back inward. Such part of leak preventer 10b that covers the upper side surface of absorber 12b, the outwardly folded-back part and the inwardly folded-back part configure surface sheet 14i, and absorber 12b is covered, except for the center part thereof.

Accordingly, the cross-sectional area of the transferring passage for bodily fluids, which is formed through the coupling between this surface sheet and the hanging parts, is further increased, and thus, the capacity to envelop the bodily fluids and to temporarily store them can also be further increased.

It should be noted that, in the respective absorbent articles shown in FIG. 4, since the center part of the upper side surface of the absorber in the lateral direction is not covered by the surface sheet, it is preferable to have the absorber being covered by a core wrapping sheet in order to keep the shape of the absorber and to prevent the occurrence of dust or SAP droppage.

FIG. 5 contains schematic diagrams of the absorbent article according to the present invention with various surface sheets. The surface sheets shown in FIG. 5 have a leak preventer in sheet form being integrated with an absorber in sheet form and being folded so as to leave a gap at the center part. The center part in the lateral direction is the liquid permeable area and the right and left sides of the liquid permeable area of the surface sheet are the liquid impermeable areas.

An example of the absorber in sheet form to be used in these surface sheets includes a super absorbent composite sheet, which is proposed by the present inventors in JP2008-136583A. Such super absorbent composite sheet includes: an SAP support layer (for example, a non-woven fabric supporting SAP) having a liquid component absorbing power; an absorption/diffusion layer (for example, tissue) stacked on the SAP support layer and having hydrophilicity; and a hydrophobic surface layer (for example, a water-resistant non-woven fabric layer such as a water-resistant SMS non-woven fabric layer or a water-resistant SB non-woven fabric layer) stacked on the absorption/diffusion layer and having water resistance, and these layers are integrated together. This super absorbent composite sheet can be configured without using wood pulp.

Since wood pulp is not used in this sheet-form absorber, the SAP content is extremely high and thus, the absorption speed is low and blockage is likely to occur. The excreted bodily fluids need to be distributed over the entire absorber as soon as possible, and thus, since the distribution of the bodily fluids in this type of surface sheet is fast, it is preferably used in combination with this sheet-form absorber.

FIG. 5(A) is a schematic lateral end view of the absorbent article according to the present invention.

Absorbent article 100j shown in FIG. 5(A) has leak preventer 10c with the right and left sides thereof being folded inward such that absorber 12c formed thereon in a stripe pattern is encompassed inside. The folded parts cover the absorber 12c, as surface sheet 14j, except for the center part thereof.

FIG. 5(B) is a schematic lateral end view of the constituent materials of surface sheet 14j and absorber 12c.

As shown in FIG. 5(B), core wrapping sheet 12c" is stacked on the upper side of the SAP support layer of super absorbent composite sheet 11, which includes: non-woven fabric 12c' that supports SAP formed in a stripe pattern and that configures the SAP support layer; tissue 11" that is stacked on the underside of the SAP support layer and that configures the absorption/diffusion layer having hydrophilicity; and water-resistant non-woven fabric layer 11' that is stacked on the underside of the absorption/diffusion layer and that configures the hydrophobic surface layer having water resistance, and these materials are integrated together.

When the right and left sides of super absorbent composite sheet 11 and core wrapping sheet 12c" are folded such that core wrapping sheet 12c" is on the inner side, a shape assumed by surface sheet 14j and absorber 12c shown in FIG. 5(A) is obtained. More specifically, water-resistant non-woven fabric layer 11' and tissue 11" of super absorbent composite sheet 11 become leak preventer 10c on the underside and become surface sheet 14j on the upper side. In addition, core wrapping sheet 12c" and non-woven fabric 12c' that supports the SAP of super absorbent composite sheet 11 become absorber 12c.

FIG. 5(C) is a schematic lateral end view of the absorbent article according to the present invention.

Absorbent article 100k shown in FIG. 5(C) has leak preventer 10d with the right and left sides thereof being folded inward such that absorber 12d formed thereon in a stripe pattern is encompassed inside and further being folded outward. Such part folded inward and such part folded outward configure surface sheet 14k and they cover absorber 12d, except for the center part thereof.

FIG. 5(D) is a schematic lateral end view of the constituent materials of surface sheet 14k and absorber 12d.

As shown in FIG. 5(D), core wrapping sheet 12d" is stacked on the upper side of the SAP support layer of super absorbent composite sheet 11a, which includes: non-woven fabric 12d' that supports SAP formed in a stripe pattern and that configures the SAP support layer; tissue 11a" that is stacked on the underside of the SAP support layer and that configures the absorption/diffusion layer having hydrophilicity; and water-resistant non-woven fabric layer 11a' that is stacked on the underside of the absorption/diffusion layer and that configures the hydrophobic surface layer having water resistance, and these materials are integrated together. It should be noted that non-woven fabric 12d' that supports the SAP is not formed in the vicinities of the edge parts of super absorbent composite sheet 11a in the lateral direction.

In place of super absorbent composite sheet 11a, similarly to super absorbent composite sheet 11 shown in FIG. 5(B), a composite sheet having a structure similar to that of super absorbent composite sheet 11a may be used, wherein a super absorbent composite sheet having the non-woven fabric supporting the SAP formed to the edge parts thereof in the lateral direction and a layer of leak prevention sheet with the width thereof in the lateral direction being wider than that of the super absorbent composite sheet are joined to the underside of the super absorbent composite sheet.

When the right and left sides of super absorbent composite sheet 11a and core wrapping sheet 12d" are folded such that core wrapping sheet 12d" is on the inner side and further folded outward, surface sheet 14k and absorber 12d shown in FIG. 5(C) can be obtained. More specifically, water-resistant non-woven fabric layer 11a' and tissue 11a" of super absorbent composite sheet 11a become leak preventer 10d on the underside and become surface sheet 14k on the upper side. In addition, core wrapping sheet 12d" and non-woven fabric 12d' that supports the SAP of super absorbent composite sheet 11a become absorber 12d. It should be noted that the parts that serve as surface sheet 14k correspond to the parts on the right and left edges of super absorbent composite sheet 11a where no absorber 12d is present in FIG. 5(D).

All of FIGS. 6 to 8 are schematic lateral end views illustrating various forms of coupling between the hanging parts of the FLGs and the surface sheet.

FIG. 6 shows forms of coupling between the hanging parts of the FLGs and the surface sheet in the absorbent article having such surface sheet, in which the center part thereof in the lateral direction is the liquid impermeable area and the right and left sides of the liquid impermeable area are the liquid permeable areas.

In FIG. 6(A), the pair of right and left FLGs 16a are arranged such that both head parts 18a face outward and both hanging parts 20a face inward. Hanging parts 20a of the pair of right and left FLGs 16a are arranged opposite to each other with a gap therebetween and thus, the inwardly-closed type form is assumed.

The outer parts of hanging parts 20a in the vicinities of the lower ends thereof are coupled to surface sheet 14c shown in FIG. 3(C) at coupling parts 26a. Surface sheet 14c is present between coupling parts 26a of hanging parts 20a of the pair of right and left FLGs 16a and surface sheet 14c (and also over the right and left edge ends of the absorbent article body). Coupling parts 26a are provided in the vicinities of the right and left edge parts of sealing film 14c" that configures the liquid impermeable area, which is on the underside of aperture film 14c' of surface sheet 14c.

In this way, a narrow and deep transferring passage P for bodily fluids is formed, which is configured by the side surfaces formed by the pair of right and left hanging parts 20a and the bottom surface formed by the liquid impermeable area of surface sheet 14c, and which thus has a small width in the lateral direction and tall side surfaces.

In the present invention, when the center part of the surface sheet in the lateral direction is the liquid impermeable area and both sides thereof are the liquid permeable areas, an embodiment in which the hanging parts of the pair of right and left FLGs are respectively coupled to the liquid permeable areas on the right and left sides of the surface sheet is also feasible.

In FIG. 6(B), the pair of right and left FLGs 16b are arranged such that both head parts 18b face inward and both hanging parts 20b face outward. Head parts 18b of the pair of right and left FLGs 16b are arranged opposite to each other with a gap therebetween and thus, the outwardly-open type form is assumed.

The inner parts of hanging parts 20b in the vicinities of the lower ends thereof are coupled to surface sheet 14l at coupling parts 26b. Surface sheet 14l is present between coupling parts 26b of hanging parts 20b of the pair of right and left FLGs 16b and surface sheet 14l (and also over the right and left edge ends of the absorbent article body). Surface sheet 14l is basically similar to surface sheet 14c; however, the width in the lateral direction of sealing film 14l'" which is present on the underside of apertured film 14l' is larger. Coupling parts 26b are provided in the vicinities of the right and left edge parts of sealing film 14l'" that configures the liquid impermeable area, which is on the underside of aperture film 14l' of surface sheet 14l.

In this way, a wide and shallow transferring passage P for bodily fluids is formed, which is configured by the side surfaces formed by the pair of right and left hanging parts 20b and the bottom surface formed by the liquid impermeable area of surface sheet 14l, and which thus has a large width in the lateral direction and low side surfaces.

FIG. 7 shows forms of coupling between the hanging parts of the FLGs and the surface sheet in the absorbent article, such surface sheet being the one shown in FIG. 4(A) or FIG. 4(B) (i.e. the surface sheet formed with a center part aperture and which is integrated with the leak preventer), and wherein a leak preventer which is folded back on the upper side surface of the absorber from external sides of the right and left edge parts thereof so as to cover such absorber, except for the center part thereof. In this embodiment, the bottom surface of the transferring passage for bodily fluids shares the leak-preventive surface sheet parts on the right and left sides and a liquid permeable part which is present between the surface sheet parts. The excreted bodily fluids transfer over the surface of the surface sheet and are absorbed into the absorber from the liquid permeable part.

In FIG. 7(A), the pair of right and left FLGs 16c are arranged such that both head parts 18c face inward and both hanging parts 20c face outward. The head parts 18c of the pair of right and left FLGs 16c are arranged opposite to each other with a gap therebetween and thus, the outwardly-open type form is assumed.

Leak preventer 10b being folded back on the upper side surface of absorber 12b from external sides of the right and left edge parts thereof so as to cover such absorber 12b, except for the center part thereof, configures surface sheet 14g shown in FIG. 4(A).

The inner parts of hanging parts 20c in the vicinities of the lower ends thereof are coupled to surface sheet 14g at coupling parts 26c. Each of hanging parts 20c of the pair of right and left FLGs 16c is coupled to a part of surface sheet 14g which keeps a distance from the center part of absorber 12b. The part between the edge part of the center part of surface sheet 14g and coupling part 26b is used for transferring bodily fluids in the front-rear direction.

In this way, a wide and shallow transferring passage P for bodily fluids is formed, which is configured by the side surfaces formed by the pair of right and left hanging parts 20c and the bottom surface formed by the liquid impermeable areas on the right and left sides of surface sheet 14g and the liquid permeable part that is present between the liquid impermeable areas, and which thus has a large width in the lateral direction and low side surfaces.

The excreted bodily fluids transfer over the surface of surface sheet 14g within transferring passage P for bodily fluids and are absorbed into absorber 12b from the liquid permeable part.

In FIG. 7(B), the pair of right and left FLGs 16d are arranged such that both head parts 18d face outward and hanging parts 20d face inward. Hanging parts 20d of the pair of right and left FLGs 16d are arranged opposite to each other with a gap therebetween and thus, the inwardly-closed type form is assumed.

Leak preventer 10b is folded back on the upper side surface of absorber 12b from external sides of the right and left edge parts thereof so as to cover such absorber 12b, except for the center part thereof, and is further folded back outward. Such covered part and such folded-back part configure surface sheet 14h shown in FIG. 4(B).

The outer parts of hanging parts 20d in the vicinities of the lower ends thereof couple to surface sheet 14h at coupling parts 26d. Each hanging part 20d of the pair of right and left FLGs 16d is coupled to the vicinity of the outer edge of the outwardly folded-back part of surface sheet 14h. The part between the edge part of the center part of surface sheet 14h and coupling part 26d is used for transferring bodily fluids in the front-rear direction.

In this way, a narrow and deep transferring passage P for bodily fluids is formed, which is configured by the side surfaces formed by the pair of right and left hanging parts 20d and the bottom surface formed by the liquid impermeable areas on the right and left sides of surface sheet 14h and the liquid permeable part between the liquid impermeable areas, and which thus has a small width in the lateral direction and tall side surfaces. Since this transferring passage P for bodily fluids is formed by the folded-back parts of surface sheet 14h, such folded-back parts of surface sheet 14h can be deformed such that a deeper passage can be obtained by being pulled upward, via hanging parts 20d, by head parts 18d of the floating FLGs 16d.

The excreted bodily fluids transfer over the surfaces of the parts of surface sheet 14h, which are on the inner side of coupling parts 26d, in transferring passage P for bodily fluids and are absorbed into absorber 12b from the liquid permeable part.

FIG. 8 shows forms of coupling between the hanging parts of the FLGs and the surface sheet in the absorbent article, such surface sheet being the surface sheet shown in FIG. 5(C) in which a sheet-form leak preventer, which is integrated with the sheet-form absorber, is folded while leaving a gap at the center part. In this embodiment, the bottom surface of the transferring passage for bodily fluids shares the leak-preventive surface sheet parts on the right and left sides and a liquid permeable part which is present between the surface sheet parts. The excreted bodily fluids transfer over the surface of the surface sheet and are absorbed into the absorber from the liquid permeable part. In addition, since the leak preventer/surface sheet and the sheet-form absorber are integrated together, the number of constituent materials is small and the resulting the product is thin.

In FIG. 8(A), the pair of right and left FLGs 16e are arranged such that both head parts 18e face inward and both hanging parts 20e face outward. Head parts 18e of the pair of right and left FLGs 16e are arranged opposite to each other with a gap therebetween and thus, the outwardly-open type form is assumed.

The right and left sides of leak preventer 10d are folded inward such that absorber 12d, configured by core wrapping sheet 12d" and non-woven fabric 12d' that supports the SAP formed thereon in a stripe pattern, is encompassed inside. Leak preventer 10d covers absorber 12d, except for the center part thereof, and is further folded back outward. Such inwardly folded-back part and the outwardly folded-back part configure surface sheet 14k shown in FIG. 5(C).

The inner parts of hanging parts 20e in the vicinities of the lower ends thereof are coupled to surface sheet 14k at coupling parts 26e. Each hanging part 20e of the pair of right and left FLGs 16e is coupled to the vicinity of the outer edge of the outwardly folded-back part of surface sheet 14k. The part between the edge part of the center part of surface sheet 14k and coupling part 26e is used for transferring bodily fluids in the front-rear direction.

In this way, a wide and shallow transferring passage P for bodily fluids is formed, which is configured by the side surfaces formed by the pair of right and left hanging parts 20e and the bottom surface formed by the liquid impermeable areas on the right and left sides of surface sheet 14k and a liquid permeable part which is present between the liquid impermeable areas, and which thus has a large width in the lateral direction and low side surfaces. Since this transferring passage P for bodily fluids is formed by the folded-back parts of surface sheet 14k, such folded-back parts of surface sheet 14k can be deformed such that a deeper passage can be obtained by being pulled upward, via hanging parts 20e, by head parts 18e of the floating FLGs 16e.

The excreted bodily fluids transfer over the surface of surface sheet 14k in transferring passage P for bodily fluids and are absorbed into absorber 12d from the liquid permeable part.

In FIG. 8(B), the pair of right and left FLGs 16f are arranged such that both head parts 18f face outward and both hanging parts 20f face inward. Hanging parts 20f of the pair of right and left FLGs 16f are arranged opposite to each other with a gap therebetween and thus, the inwardly-closed type form is assumed.

The right and left sides of leak preventer 10d are folded inward such that absorber 12e, configured by core wrapping sheet 12e″ and non-woven fabric 12e′ that supports the SAP formed thereon in a stripe pattern, is encompassed inside. Leak preventer 10d covers absorber 12e, except for the center part thereof, and is further folded back outward. Such inwardly folded-back part and such outwardly folded-back part configure surface sheet 14m. Surface sheet 14m is basically similar to surface sheet 14k; however, the width in the lateral direction of the outwardly folded-back part is smaller.

The outer part hanging parts 20f in the vicinities of the lower ends thereof are coupled to surface sheet 14m at coupling parts 26f. Each hanging part 20f of the pair of right and left FLGs 16f is coupled to the vicinity of the outer edge of the outwardly folded-back part of surface sheet 14m. The part between the edge part of the center part of surface sheet 14m and coupling part 26f is used for transferring bodily fluids in the front-rear direction.

In this way, a narrow and deep transferring passage P for bodily fluids is formed, which is configured by the side surfaces formed by the pair of right and left hanging parts 20f and the bottom surface formed by the liquid impermeable areas on the right and left sides of surface sheet 14m and a liquid permeable part which is present between the liquid impermeable areas, and which thus has a small width in the lateral direction and tall side surfaces. Since this transferring passage P for bodily fluids is formed by the folded-back parts of surface sheet 14m, such folded-back parts of surface sheet 14m can be deformed such that a deeper passage is obtained by being pulled upward, via hanging parts 20f, by head parts 18f of the floating FLGs 16f.

The excreted bodily fluids transfer over the surface of surface sheet 14m in transferring passage P for bodily fluids and are absorbed into absorber 12e from the liquid permeable part.

The absorbent article according to the present invention is further provided with a support sheet which is present on the upper side of the surface sheet. In one of the preferred embodiments, such support sheet is coupled to the hanging parts of the pair of right and left floating leg gathers and thus, a second transferring passage for bodily fluids is formed by the hanging parts and the support sheet.

FIG. 9 contains schematic lateral end views illustrating various forms of coupling among the hanging parts of the FLGs, the surface sheet and the support sheet.

In FIG. 9(A), the pair of right and left FLGs 16g are arranged such that both head parts 18g face outward and both hanging parts 20g face inward. Hanging parts 20g of the pair of right and left FLGs 16g are arranged opposite to each other with a gap therebetween and thus, the inwardly-closed type form is assumed.

Leak preventer 10b covers absorber 12b, except for the center part thereof, by being folded inward on the upper side surface of absorber 12b from external sides of the right and left edge parts of absorber 12b and is further folded outward. Such inwardly folded-back part and such outwardly folded-back part configure surface sheet 14h shown in FIG. 4(B).

The outer parts of hanging parts 20g in the vicinities of the lower ends thereof are coupled to surface sheet 14h, via support sheet 32, at coupling parts 26g. More specifically, hanging parts 20g of the pair of right and left FLGs 16g couple to the right and left edge parts of support sheet 32 on the upper side surface thereof at coupling parts 26g″. The right and left edge parts of support sheet 32 couple, on the underside surface thereof, to the vicinities of the outer edges of the outwardly folded-back parts of surface sheet 14h at coupling parts 26g′. Thus, hanging parts 20g are indirectly coupled to surface sheet 14h by means of coupling parts 26g.

In this way, transferring passage P for bodily fluids is formed, which is configured by the bottom surface formed by the liquid impermeable areas on the right and left sides of surface sheet 14h and the liquid permeable part which is present between the liquid impermeable areas.

The excreted bodily fluids transfer over the surfaces of the parts of surface sheet 14h, which are on the inner side of coupling parts 26g, in transferring passage P for bodily fluids and are absorbed into absorber 12b from the liquid permeable part.

In addition, second transferring passage P2 for bodily fluids is formed, which is configured by the side surfaces formed by the pair of right and left hanging parts 20g and the bottom surface formed by support sheet 32.

The excreted bodily fluids transfer over the upper surface of support sheet 32 within second transferring passage P2 for bodily fluids.

The double structure consisting of the above-described transferring passage P for bodily fluids and second transferring passage P2 for bodily fluids (hereinafter simply referred to as a "double structure") is not formed over the entire length of the FLGs from front body F to rear body R via crotch part C; but rather, in one of the preferred embodiments, such double structure is partially provided between crotch part C and front body F.

In addition, both the area in which the double structure is present and the area in which transferring passage P for bodily fluids is present alone, may be present in the front-rear direction of the absorbent article.

In FIG. 9(B), the pair of right and left FLGs 16h are arranged such that both head parts 18h face inward and both hanging parts 20h face outward. Head parts 20h of the pair of right and left FLGs 16h are arranged opposite to each other with a gap therebetween and thus, the outwardly-open type form is assumed.

The right and left sides of leak preventer 10d are folded inward such that absorber 12d, configured by core wrapping sheet 12d″ and non-woven fabric 12d′ that supports the SAP formed thereon in a stripe pattern, is encompassed inside. Leak preventer 10d covers absorber 12d, except for the center part thereof, and is further folded outward. Such outwardly folded-back part and such inwardly folded-back part configure surface sheet 14k shown in FIG. 5(C).

The outer parts of hanging parts 20h in the vicinities of the lower ends thereof are coupled to surface sheet 14k, via support sheet 32a, at coupling parts 26h. More specifically, hanging parts 20h of the pair of right and left FLGs 16h couple to the right and left edge parts of support sheet 32a on the upper side surface thereof at coupling parts 26h″. The right and left edge parts of support sheet 32a couple, on the underside surface thereof, to the vicinities of the outer edges of outwardly folded-back parts of surface sheet 14k at coupling parts 26h′. Thus, hanging parts 20h are indirectly coupled to surface sheet 14k by means of coupling parts 26h.

In this way, transferring passage P for bodily fluids is formed, which is configured by the bottom surface formed by the liquid impermeable areas on the right and left sides of surface sheet 14k and a liquid permeable part which is present between the liquid impermeable areas.

The excreted bodily fluids transfer over the surface of the part of surface sheet 14k, which is on the inner side of coupling parts 26h, in transferring passage P for bodily fluids and are absorbed into absorber 12d from the liquid permeable part.

In addition, second transferring passage P2 for bodily fluids is formed, which is configured by the side surfaces formed by the pair of right and left hanging parts 20h and the bottom surface formed by support sheet 32a.

The excreted bodily fluids transfer over the upper surface of support sheet 32a within second transferring passage P2 for bodily fluids.

The above-described double structure is not formed over the entire length of the FLGs from front body F to rear body R via crotch part C; but rather, in one of the preferred embodiments, such double structure is partially provided between crotch part C and front body F.

In addition, both the area in which the double structure is present and the area in which transferring passage P for bodily fluids is present alone, may be present in the front-rear direction of the absorbent article. In such case, the area in which second transferring passage P2 for bodily fluids, such as shown in FIG. 9(C) described below, is present alone may also be provided.

In FIG. 9(C), the pair of right and left FLGs 16i are arranged such that both head parts 18i face inward and both hanging parts 20i face outward. Head parts 20i of the pair of right and left FLGs 16i are arranged opposite to each other with a gap therebetween and thus, the outwardly-open type form is assumed.

The right and left sides of leak preventer 10d are folded inward such that absorber 12d, configured by core wrapping sheet 12d'' and non-woven fabric 12d' that supports the SAP formed thereon in a stripe pattern, is encompassed inside. Leak preventer 10d covers absorber 12d, except for the center part thereof, and is further folded outward. Such inwardly folded-back part and such outwardly folded-back part configure surface sheet 14k shown in FIG. 5(C).

The outer parts of hanging parts 20i in the vicinities of the lower ends thereof are coupled to support sheet 32b at coupling parts 26i.

In this way, second transferring passage P2 for bodily fluids is formed, which is configured by the side surfaces formed by the pair of right and left hanging parts 20i and the bottom surface formed by support sheet 32b.

The excreted bodily fluids transfer over the upper surface of support sheet 32b in second transferring passage P2 for bodily fluids.

When the absorbent article according to the present invention includes the area in which second transferring passage P2 for bodily fluids is present alone, second transferring passage P2 for bodily fluids assumes a state in which it is floated from the absorbent article body and this leads to a better fitting of the absorbent article according to the present invention to the wearer.

In the front-rear direction of the absorbent article, along with the area where the above-described second transferring passage P2 for bodily fluids is present alone, the area in which transferring passage P for bodily fluids is present alone and/or the area in which the double structure is present may also be provided.

In this case, the excreted bodily fluids transfer and are rectified over the upper surface of support sheet 32b in second transferring passage P2 for bodily fluids, and subsequently, the bodily fluids transfer from front and rear exits of second transferring passage P2 for bodily fluids to transferring passage P for bodily fluids in the area where such transferring passage P for bodily fluids is present alone and/or the area where the double structure is present. The bodily fluids then transfer through transferring passage P for bodily fluids to be absorbed by the absorber in a smooth manner. This point will be explained in the respective absorbent articles shown in FIGS. 12 and 13 below.

FIG. 10 contains schematic plan view illustrating various support sheet configurations. In the description below, the size of the support sheet has numerical values intended for a medium-sized diaper for infants (approximately 6 kg or more in body weight); however, the present invention is not limited thereto.

Support sheet 34 shown in FIG. 10(A) is rectangular, and length L in the front-rear direction is shorter than width W in the lateral direction. In other words, the width in the lateral direction is longer than the length in the front-rear direction. Length L in the front-rear direction is preferably approximately 20 to 70 mm and width W in the lateral direction is preferably approximately 30 to 130 mm.

Support sheet 34 has: coupling parts 36 with respect to the hanging parts in the vicinities of the right and left edge parts over substantially the entire length in the front-rear direction; and coupling part 38 with respect to the surface of the surface sheet or the absorber in the vicinity of the center in the lateral direction over substantially the entire length in the front-rear direction. In the present invention, as described above, it is preferred that the support sheet has a coupling part with respect to the surface of the surface sheet or the absorber.

Support sheet 34a shown in FIG. 10(B) is rectangular, and the length in the front-rear direction is longer than the width in the lateral direction. The length in the front-rear direction is preferably approximately 100 to 250 mm and the width in the lateral direction is preferably approximately 30 to 130 mm.

Support sheet 34a has: coupling parts 36a with respect to the hanging parts in the vicinities of the right and left edge parts over substantially the entire length in the front-rear direction; and two coupling parts 38a with respect to the surface of the surface sheet or the absorber, in the vicinities of the front end and the rear end, in the vicinity of the center in the lateral direction.

Support sheet 34b shown in FIG. 10(C) has a deformed rectangular shape, and the length in the front-rear direction is longer than the width in the lateral direction. The length in the front-rear direction is preferably approximately 120 to 300 mm. The width in the lateral direction is preferably approximately 30 to 130 mm. More specifically, apexes are formed at the center parts of the front end and the rear end, and thus, a hexagonal shape is obtained.

Support sheet 34b has: coupling parts 36b with respect to the hanging parts in the vicinities of the right and left edge parts over substantially the entire length in the front-rear direction; and three coupling parts 38b with respect to the surface of the surface sheet or the absorber, in the vicinities of the front end, the rear end and the center part, in the vicinity of the center in the lateral direction. The number of coupling parts with respect to the surface of the absorber may be one, two, four, or more.

Support sheet 34c shown in FIG. 10(D) has a deformed rectangular shape, and the length in the front-rear direction is longer than the width in the lateral direction. The length in the front-rear direction is preferably approximately 120 to 300 mm. The width in the lateral direction is preferably approximately 30 to 130 mm. More specifically, the center parts of the front end and the rear end are convexly curved.

At the center part in the front-rear direction, support sheet 34*c* is provided with slit 40 in a C shape, and the part surrounded by slit 40 can bend downward to the underside. This bent-down part serves as an exit of the second transferring passage for bodily fluids.

Support sheet 34*c* has: coupling parts 36*c* with respect to the hanging parts in the vicinities of the right and left edge parts over substantially the entire length in the front-rear direction; and three coupling parts 38*c* with respect to the surface of the surface sheet or the absorber in the vicinities of the front end and the rear end and at the part surrounded by slit 40, in the vicinity of the center in the lateral direction.

Support sheet 34*c* is preferably arranged from the front end part to the rear end part of the absorbent article in the length direction through the front body, the crotch part and the rear body.

Support sheet 34*d* shown in FIG. 10(E) has a deformed rectangular shape, and the length in the front-rear direction is longer than the width in the lateral direction. The length in the front-rear direction is preferably approximately 100 to 150 mm. The width in the lateral direction is preferably approximately 30 to 130 mm. More specifically, the center part in the rear end is convexly curved and also has notch 42.

Support sheet 34*d* has: coupling parts 36*d* with respect to the hanging parts in the vicinities of the right and left edge parts over substantially the entire length in the front-rear direction; and a total of three coupling parts 38*d* with respect to the surface of the surface sheet or the absorber, in the vicinity of the front end, in the vicinity of the center in the lateral direction, and at both sides of notch 42 in the vicinity of the rear end. The vicinity of notch 42 functions as an exit of the second transferring passage for bodily fluids.

The support sheet couples to the pair of right and left hanging parts and forms second transferring passage P2 for bodily fluids, wherein the hanging parts serve as the right and left side surfaces and the support sheet serves as the bottom surface. Thus, it is preferred that urine does not leak from second transferring passage P2 for bodily fluids to transferring passage P for bodily fluids. Accordingly, the material of the support sheet is preferably a hydrophobic material with a leak prevention property. Examples include: a PP or PE-based spunmelt non-woven fabric; and soft synthetic resin films made of PE, PP, EVA, polyurethane or the like.

On the other hand, the support sheet preferably has a hydrophilic surface for a smooth transferring (fast and uniform transferring) of urine.

In view of the points above, it is one of the preferred embodiments to make the support sheet from a composite material in which a hydrophobic material and a hydrophilic material are combined.

Examples of compounding methods for combining a hydrophobic material and a hydrophilic material include lamination, coating, and binding together using an adhesive.

Examples of compound support sheet in which a hydrophobic material and a hydrophilic material are combined include a support sheet in which an SMS non-woven fabric made of PP and a PE film are bound together, a laminate of tissue and a PE film and a laminate of a rayon non-woven fabric and an EVA film.

The entirety or alternatively only a part thereof, of the support sheet in the front-rear direction and in the lateral direction may be compounded with a hydrophobic material and a hydrophilic material.

The absorbent articles according to the present invention will now be explained more specifically below, based on embodiments.

FIG. 11 contains schematic diagrams of an embodiment of the absorbent article according to the present invention. FIG. 11(A) is a developed plan view which schematically shows the state in which an absorbent article, in the form of an underpants-type diaper, is cut along the right and left side parts (denoted with "Z" and "Z'" in the figure) of the waist gather and in which stress is applied to the absorbent article such that it is pulled in the front-rear direction and the lateral direction so as to be developed into a substantially planar form. FIG. 11(B) is a lateral end view along line XIB-XIB in FIG. 11(A) when stress is not applied to the absorbent article (i.e. in a relaxed state).

Absorbent article 102 of the present invention shown in FIG. 11 is configured as an underpants-type diaper, and is basically provided with: leak preventer 10*d* in sheet form; absorber 12*d* capable of absorbing a bodily fluid, wherein at least one layer thereof is arranged above leak preventer 10*d*; surface sheet 14*k* that covers the entire upper surface of absorber 12*d* and that has a liquid impermeable area at a part thereof; and a pair of right and left FLGs 16*e* arranged, above absorber 12*d*, from a front end part of the absorbent article body to a rear end part thereof in a longitudinal direction, via front body F, crotch part C and rear body R.

The details of leak preventer 10*d*, absorber 12*d* and surface sheet 14*k* are as described with reference to FIG. 5(C). The relationship between these elements and FLGs 16*e* is as described with reference to FIG. 8(A) and thus, the outwardly-open type form is assumed.

More specifically, for leak preventer 10*d*, absorber 12*d* and surface sheet 14*k*, a combination in which a laminated body, wherein a sheet having an air permeable PE film (with a thickness of, for example, 20 μm) and a PE/PP-based spunbond non-woven fabric (having a basis weight of, for example, 15 g/m$^2$ (manufactured by, for example, Chisso Corporation)) compounded therein is laminated onto a sheet-form absorber (for example, MegaThin (registered trademark) manufactured by Japan Absorbent Technology Institute (having a basis weight of 180 g/m$^2$)), is combined with an apertured film made of PE (having a basis weight of, for example, 15 g/m$^2$ (for example, DRY WEAVE, manufactured by TREDEGAR Corporation)) as core wrapping sheet 12*d'''* may preferably be used. For the sheet-form absorber, the above-described super absorbent composite sheet may preferably be used.

Absorbent article 102 according to the present invention is provided with two types of leg gathers. In particular, in addition to the above-described FLGs 16*e*, OLGs 31 are provided, which are present in the side edge parts of the absorbent article body. OLGs 31 are configured such that three parallel polyurethane filaments (stretchable members) are joined between the folded-back non-woven fabric parts and are provided such that they are next to the side edge parts of the bottom surface of leak preventer 10*d* which is folded back along with absorber 12*d*.

In absorbent article 102, external covering sheet 44 is provided on the underside of leak preventer 10*d*.

External covering sheet 44 is a member that is used in an underpants-type diaper and that bears a fitting function of enfolding the wearer's body. Specifically, a sheet-form member forming the respective parts of front body F, crotch part C and rear body R is used.

In an underpants-type diaper such as absorbent article 102, since leak preventer 10d prevents the leakage of urine or the like, it is unnecessary to use liquid impermeable materials for external covering sheet 44. For example, for external covering sheet 44, any external covering sheet that is used in publicly-known conventional absorbent articles may be used. In particular, a non-woven fabric configured by synthetic fibers made of, for example, polyethylene, polypropylene, polyester, or other thermoplastic resin may be used as external covering sheet 44.

In absorbent article 102, external covering sheet 44 configures shining gather 46 by sandwiching a stretchable member (for example, polyurethane filaments) between two pieces of non-woven fabric. Shining gathers 46 are provided at positions where they cover the abdominal area and the back area of the wearer at the time of wearing. In the present invention, the configuration of the shining gathers is not particularly limited and, for example, a publicly-known conventional configuration of the shining gathers may be used.

Absorbent article 102 of the present invention is further provided with waist gathers 48 in the vicinity of the front end and the vicinity of the rear end of leak preventer 10d.

Waist gather 48 serves as a fixing band that connects the front end part of the body of absorbent article 102 to the rear end part thereof, attaches the diaper closely around the waist and prevents the absorbent article from sliding down. Waist gather 48 is formed by covering a stretchable member (for example, polyurethane filaments) with a non-woven fabric.

In the present invention, the configuration of the waist gather is not particularly limited and, for example, a publicly-known conventional waist gather may be used. Specifically, examples of such configuration include a configuration in which it is formed by covering a stretchable member (for example, polyurethane filaments) with a non-woven fabric, as in absorbent article 102, and a configuration in which it is formed by folding back the front end part and the rear end part of the external covering sheet, on the upper side, so as to cover the stretchable member (for example, polyurethane filaments).

Head parts 18e of the pair of right and left FLGs 16e oppose to each other with a gap of approximately 40 mm therebetween.

FLG 16e is fixed to the front end and the rear end of the diaper body at corresponding front end coupling part 23 and rear end coupling part 25. The length of front end coupling part 23 and rear end coupling part 25 along hanging part 20e is longer than that along head part 18e, and they extend to a part of the surface of absorber 12d (i.e. the surface of surface sheet 14k) in front body F and rear body R.

Head parts 18e of FLGs 16e are not fixed in most part of front body F, in crotch part C, and in most part of rear body R, and are maintained in a floating condition.

The lower ends of hanging parts 20e of FLGs 16e are coupled to the side edge parts of the outwardly folded-back parts of surface sheet 14k at coupling parts 26e. Each coupling part 26e is connected to front end coupling part 23 on the front body side and to rear end coupling part 25 on the rear body side, and extends over the entire length of hanging part 20e. In this way, in absorbent article 102, the interior space of the pair of right and left FLGs 16e is sealed off, except for the opening formed between the pair of right and left head parts 18e for receiving bodily fluids, and thus, a capsule-shaped configuration without an exit for bodily fluids is obtained.

In the front end part and the rear end part of the diaper body, front part corner pocket 50 and rear part corner pocket 52 are formed, which are configured through coupling between the pair of right and left FLGs 16e and the surface of surface sheet 14k.

End caps which extend from the waist band configured by shirring gathers 46 or the like are provided above front part corner pocket 50 and rear part corner pocket 52. The end caps also cover the gaps between the right and left corner pockets, and thus, sealing is achieved such that leakage of bodily fluids from the upper and lower end parts is prevented.

OLGs 31 are provided on the right and left edge parts of the diaper body.

When urine is excreted onto this diaper, such urine is received through the opening between head parts 18e of the pair of right and left FLGs 16e, and the total volume thereof is accommodated in transferring passage P for bodily fluids, which is present over the entire length from front body F to rear body R through crotch part C and which is provided with absorber 12d in the center part in the lateral direction and outwardly folded-back parts of surface sheet 14k on the right and left sides of absorber 12d.

The urine accommodated in transferring passage P for bodily fluids is absorbed by absorber 12d, which is exposed in the center in the lateral direction, and also transfers to the front and to the rear over the liquid impermeable parts formed by surface sheet 14k. As described above, since transferring passage P for bodily fluids is not provided with an exit, substantially all of the volume of the urine will be absorbed by absorber 12d as it transfers to the front and to the rear.

Only a small portion of the excreted urine, which is attached to the bottom surface of transferring passage P for bodily fluids, is likely to make contact with the wearer's skin. In addition, head parts 18e of FLGs 16e and hanging parts 20e of FLGs 16e that form the side surfaces of transferring passage P for bodily fluids serve as barriers. Accordingly, the chances of the wearer's skin making contact with the urine are significantly reduced over the entire duration of use (i.e. the life-time) of the diaper from the beginning to the end of use of such diaper, and the occurrence of hot and stuffy state and rashes is also suppressed.

Next, the cases of when feces are excreted will be described.

Similarly to the case with urine, the excreted feces are received through the opening between head parts 18e of the pair of right and left FLGs 16e, are guided by hanging parts 20e into transferring passage P for bodily fluids, and are accommodated in transferring passage P for bodily fluids, which is provided with absorber 12d in the center part in the lateral direction and outwardly folded-back parts of surface sheet 14k on the right and left sides of absorber 12d.

When the feces are solid, they stay as is at the position (in many cases, in the vicinity of the center in the lateral direction) where they are accommodated. However, when the feces are watery, they spread over absorber 12d and the water content is absorbed by absorber 12d and the solid content remains on the surface of absorber 12d and/or on the surface of surface sheet 14k.

Contact between the excreted feces and the wearer's skin is significantly suppressed as compared to the conventional diaper, since the head parts and the hanging parts of the FLGs serve as a physical obstacle to the wearer's skin making contact with the surface of the absorber. In particular, when the feces are solid, only the periphery of the anus becomes dirty and thus, the burden of the care-taker of cleaning can be reduced when this diaper is used for, for example, the elderly.

FIG. 12 contains schematic diagrams of another embodiment of the absorbent article according to the present invention.

FIG. 12(A) is a developed plan view which schematically shows the state in which an absorbent article, in the form of an underpants-type diaper, is cut along the right and left side parts (denoted with Z-Z' in the figure) of the waist gather and in which stress is applied to the absorbent article such that it is pulled in the front-rear direction and the lateral direction so as to be developed into a substantially planar form. FIG. 12(B) is a lateral end view along line XIIB-XIIB in FIG. 12(A) when stress is not applied to the absorbent article (i.e. in a relaxed state). FIG. 12(C) is a lateral end view along line XIIC-XIIC in FIG. 12(A) when stress is not applied to the absorbent article (i.e. in a relaxed state).

Absorbent article 104 of the present invention shown in FIG. 12 is configured as an underpants-type diaper for infants and is basically similar to absorbent article 102 shown in FIG. 11; however, it differs therefrom with respect to the point that support sheet 34a is further provided.

Support sheet 34a is rectangular, as shown in FIG. 10(B), and the length in the front-rear direction is approximately 110 mm and the width in the lateral direction is approximately 120 mm. However, coupling part 38e with respect to the surface of absorber 12d is present at only one location in the vicinity of the rear end, in the vicinity of the center in the lateral direction.

The details of leak preventer 10d, absorber 12d and surface sheet 14 are as described with reference to FIG. 5(C). The relationship among these elements, FLGs 16h and support sheet 34a is as described with reference to FIG. 9(B), and thus, the outwardly-open type form is assumed.

Head parts 18h of the pair of right and left FLGs 16h oppose to each other with a gap of approximately 40 mm therebetween.

FLG 16h is fixed to the front end and the rear end of the diaper body at corresponding front end coupling part 23 and rear end coupling part 25. The length of front end coupling part 23 and rear end coupling part 25 along hanging part 20h is longer than that along head part 18h, and they extend to a part of the surface of absorber 12d (i.e. the surface of surface sheet 14k) in front body F and rear body R.

Head parts 18h of FLGs 16h are not fixed in most part of front body F, in crotch part C, and in most part of rear body R, and are maintained in a floating condition.

The lower ends of hanging parts 20h of FLGs 16h are coupled to the upper side surfaces of the right and left edge parts of support sheet 34a, in the areas of such hanging parts in the front-rear direction where such support sheet 34a is present, at coupling parts 26h". The underside surfaces of the right and left edge parts of support sheet 34a are coupled to the side edge parts of the outwardly folded-back parts of surface sheet zone 14k at coupling parts 26h' (see FIG. 12(B)). Namely, hanging parts 20h of FLGs 16h are coupled to support sheet 34a through coupling parts 26h, each of which consists of coupling part 26h" and coupling part 26h'.

Support sheet 34a is coupled to core wrapping sheet 12d" of absorber 12d at coupling part 38e in the center part in the lateral direction.

In the areas where support sheet 34a is not present in the front-rear direction, the lower ends of hanging parts 20h of FLGs 16h are coupled to the side edge parts of the outwardly folded-back parts of surface sheet zone 14k at coupling parts 26j (see FIG. 12(C)). Each coupling part 26j is connected to front end coupling part 23 on the front body side and to rear end coupling part 25 on the rear body side.

As shown in FIG. 12(B), support sheet 34a forms second transferring passage P2 for bodily fluids, together with hanging parts 20h.

In addition, in the areas where support sheet 34a is present, transferring passage P for bodily fluids is formed: in the space between upper surfaces of the outwardly folded-back parts of surface sheet 14k present on the right and left sides, and the underside of support sheet 34a; and in the space between core wrapping sheet 12d" of absorber 12d present in the center part in the lateral direction and the underside of support sheet 34a.

Accordingly, in the areas where support sheet 34a is present, second transferring passage P2 for bodily fluids is present above transferring passage P for bodily fluids.

On the other hand, as shown in FIG. 12(C), in the areas where support sheet 34a is not present, the outwardly folded-back parts of surface sheet 14k present on the right and left sides, and core wrapping sheet 12d" of absorber 12d present in the center part in the lateral direction, form transferring passage P for bodily fluids, together with hanging parts 20h.

When urine is excreted into this diaper, such urine is received through the opening between head parts 18h of the pair of right and left FLGs 16h, and the total volume thereof is accommodated in second transferring passage P2 for bodily fluids, which is present from front body F to crotch part C.

The urine accommodated in second transferring passage P2 for bodily fluids is rectified and discharged from the rear end of second transferring passage P2 for bodily fluids, and then transfers to transferring passage P for bodily fluids.

The urine accommodated in transferring passage P for bodily fluids is absorbed by absorber 12d, which is exposed in the center in the lateral direction, and also transfers to the front and to the rear over the liquid impermeable parts formed by surface sheet 14k. Since transferring passage P for bodily fluids is not provided with an exit, substantially all of the volume of the urine will be absorbed by absorber 12s as it transfers to the front and to the rear.

Only a small portion of the excreted urine, which is attached to the bottom surface of transferring passage P for bodily fluids, is likely to make contact with the wearer's skin. In addition, head parts 18h of FLGs 16h and hanging parts 20h of FLGs 16h that form the side surfaces of transferring passage P for bodily fluids serve as barriers. Accordingly, the chances of the wearer's skin making contact with the urine are significantly reduced over the entire duration of use (i.e. the life-time) of the diaper from the beginning to the end of use of such diaper, and the occurrence of hot and stuffy state and rashes is also suppressed.

Next, the cases of when feces are excreted will be described.

Similarly to the case with urine, the excreted feces are received through the opening between head parts 18h of the pair of right and left FLGs 16h, are guided by hanging parts 20h into transferring passage P for bodily fluids, since no support sheet 34a is present in rear body R, and are accommodated in transferring passage P for bodily fluids, which is provided with absorber 12d in the center part in the lateral direction and outwardly folded-back parts of surface sheet 14k on the right and left side of absorber 12d.

When the feces are solid, they stay as is at the position (in many cases, in the vicinity of the center in the lateral direction) where they are accommodated. However, when the feces are watery, they spread over absorber 12d and the water content is absorbed by absorber 12d and the solid content remains on the surface of absorber 12d and/or on the surface of surface sheet 14k.

Contact between the excreted feces and the wearer's skin is significantly suppressed as compared to the conventional diaper, since the head parts and the hanging parts of the FLGs serve as a physical obstacle to the wearer's skin making contact with the surface of the absorber. In particular, when the feces are solid, only the periphery of the anus becomes dirty and thus, the burden of the care-taker of cleaning can be reduced when this diaper is used for, for example, the elderly.

FIG. 13 contains schematic diagrams of a further embodiment of the absorbent article according to the present invention.

FIG. 13(A) is a developed plan view which schematically shows the state in which an absorbent article, in the form of an underpants-type diaper, is cut along the right and left side parts (denoted with Z-Z' in the figure) of the waist gather and in which stress is applied to the absorbent article such that it is pulled in the front-rear direction and the lateral direction so as to be developed into a substantially planar form. FIG. 13(B) is a lateral end view along line XIIIB-XIIIB in FIG. 13(A) when stress is not applied to the absorbent article (i.e. in a relaxed state). FIG. 13(C) is a lateral end view along line XIIIC-XIIIC in FIG. 13(A) when stress is not applied to the absorbent article (i.e. in a relaxed state).

Absorbent article 106 of the present invention shown in FIG. 13 is configured as an underpants-type diaper for infants and is basically similar to absorbent article 104 shown in FIG. 12; however, the state of existence of support sheet 34a is different.

More specifically, similar to the embodiment shown in FIG. 9(C), support sheet 34a is coupled to hanging parts 20i of the pair of right and left FLGs 16i at coupling parts 26i; however, it is not coupled to surface sheet 14k (see FIG. 13(B)).

It should be noted that in the areas where support sheet 34a is not present, as with absorbent article 104, surface sheet 14k is coupled to the pair of right and left hanging parts 20i at coupling parts 26j (see FIG. 13(C)). As shown in FIG. 13(A), each coupling part 26j extends from front body F to rear body R through crotch part C, except for the area where support sheet 34a is present, and is coupled to the front end part or the rear end part of the absorbent article so as to form transferring passage P for bodily fluids.

In this way, the entire second transferring passage P2 for bodily fluids formed by support sheet 34a and hanging parts 20i floats at the crotch part, and a configuration in which the passage is spaced apart from the surface of the absorber is obtained, and thus, a better fitting of crotch part C to the wearer's body is achieved.

The behavior of when urine and feces are excreted into this diaper is substantially similar to that in absorbent article 104.

As described above, the absorbent article according to the present invention is illustrated based on the respective embodiments illustrated herein; however, it should be noted that the present invention is not limited to these embodiments and, for example, the configurations of the respective parts may be replaced with any configuration capable of performing a similar function.

In addition, the configurations of the respective parts in the respective embodiments may be combined in an arbitrary manner to obtain other embodiments.

The absorbent article according to the present invention may be preferably used for disposable diapers (for infants and adults), incontinence articles, training pants, or the like.

DESCRIPTIONS OF REFERENCE NUMERALS 1,16,16a,16b,16c,16d, 16e, 16f, 16g, 16h, 16i floating leg gathers (FLG)
2, 18, 18a, 18b, 18c, 18d, 18e, 18f, 18g, 18h, 18i head part
3, 20, 20a, 20b, 20c, 20d, 20e, 20f, 20g, 20h, 20i hanging part
4, 12, 12a, 12b, 12c, 12d, 12e, 13 absorber
5, 14, 14a, 14b, 14c, 14d, 14e, 14f, 14g, 14h, 14i, 14j, 14k, 14l, 14m surface sheet
6, 6', 26, 26a, 26b, 26c, 26d, 26e, 26f, 26g, 26g', 26g", 26h, 26h', 26h", 26i, 26j, 36,
36a, 36b, 36c, 36d, 38, 38a, 38b, 38c, 38d, 38e coupling parts
10, 10a, 10b, 10c, 10d leak preventer
11,11a super absorbent composite sheet
11',11a' water-resistant non-woven fabric layer
11",11a" tissue
12c',12d', 12e' non-woven fabric that supports the SAP
12c", 12d", 12e" core wrapping sheet
14', 14c', 14l' apertured film
14", 14c", 14l" sealing film
14a', 14b', 14d', 14e' liquid impermeable sheet
14a", 14b", 14d", 14e", 14f' liquid permeable sheet
14f' adhesion part
22,23 front end coupling part
24,25 rear end coupling part
28 detachable members
30,31 outer leg gather (OLG)
32, 32a, 32b, 34, 34a, 34b, 34c, 34d support sheet
40 slit
42 notch
44 external covering sheet
46 shining gathers
48 waist gathers
50 front part corner pocket
52 rear part corner pocket
100, 100a, 100b, 100c, 100d, 100e, 100f, 100g, 100h, 100i, 100j, 100k, 102, 104, 106 absorbent article
C crotch part
F front body
Na liquid impermeable areas
P fluid transferring passage
P2 fluid transferring passage
Pa liquid permeable areas
R rear body

The invention claimed is:

1. An absorbent article, comprising:
a leak preventer in sheet form;
an absorber configured to absorb a bodily fluid, the absorber having a top surface and a bottom surface, the bottom surface of the absorber being arranged directly adjacent to the leak preventer, the top surface of the absorber being arranged on an opposite side of the absorber from the bottom surface of the absorber;
a surface sheet located on the opposite side of the absorber from the bottom surface of the absorber and including at least one liquid impermeable area, which covers at least a part of the top surface of the absorber; and
a pair of first and second floating leg gathers coupled to the surface sheet, which covers the absorber, each of the pair of first and second floating leg gathers extending from a front end part to a rear end part of a body of the absorbent article in a length direction of the body of the absorbent article via a front body, a crotch part, and a rear body, each of the pair of first and second floating leg gathers consisting of a head part and a hanging part that connects to the head part, wherein:

a front end part and a rear end part of each of the pair of first and second floating leg gathers are respectively coupled to a vicinity of the front end part and a vicinity of the rear end part of the body of the absorbent article, the hanging part hanging down from the head part toward the absorber; and each hanging part of the pair of first and second floating leg gathers is respectively connected to the surface sheet at the crotch part and not connected to the surface sheet at portions of the front body and the rear body, such that a transfer passage for bodily fluids is formed in the crotch part by coupling each of the respective hanging parts of the pair of first and second floating leg gathers to the surface sheet, the transfer passage comprising side surfaces formed by the pair of left and right hanging parts and a bottom surface formed by the surface sheet, and the transfer passage is not formed where the hanging parts are not connected to the surface sheet.

2. The absorbent article according to claim 1, wherein:
both of the respective hanging parts of the pair of first and second floating leg gathers are respectively disposed closer to a central longitudinal axis extending length direction of the body of the absorbent article than both of the respective head parts of the pair of first and second floating leg gathers;
the respective hanging parts of the pair of first and second floating leg gathers are arranged opposite to each other relative to the central longitudinal axis with a space therebetween; and
the surface sheet is located between respective coupling parts and the absorber, the respective coupling parts being connected to the respective hanging parts of the pair of first and second floating leg gathers.

3. The absorbent article according to claim 1, wherein:
both of the respective head parts of the pair of first and second floating leg gathers are respectively disposed closer to a central longitudinal axis extending length direction of the body of the absorbent article than both of the respective hanging parts of the pair of first and second floating leg gathers;
the respective head parts of the pair of first and second floating leg gathers are arranged opposite to each other relative to the central longitudinal axis with a gap therebetween; and
the surface sheet is located between respective coupling parts and the absorber, the respective coupling parts being connected to the respective hanging parts of the pair of first and second floating leg gathers.

4. The absorbent article according to claim 1, wherein:
the surface sheet includes a pair of aperture films and a sealing film;
a center part of the surface sheet in a lateral direction includes the sealing film and is the liquid impermeable area;
the pair of aperture films are located on opposite lateral sides of the sealing film, which are liquid permeable areas; and
the respective hanging parts of the pair of first and second floating leg gathers are respectively coupled to vicinities of first and second edge parts of the liquid impermeable area of the surface sheet.

5. The absorbent article according to claim 1, wherein:
the surface sheet includes a pair of aperture films and a sealing film;
a center part of the surface sheet in a lateral direction includes the sealing film and is the liquid impermeable area;
the pair of aperture films are located on opposite lateral sides of the sealing film, which are liquid permeable areas; and
the respective hanging parts of the pair of first and second floating leg gathers are respectively coupled to the liquid permeable areas on first and second sides of the surface sheet.

6. The absorbent article according to claim 1, wherein:
the surface sheet covering the absorber is formed by folding back the leak preventer on the top surface of the absorber from external sides of first and second edge parts of the absorber; and
each of the respective hanging parts of the pair of first and second floating leg gathers is coupled to a part of the surface sheet, the part of the surface sheet being located away from a center part of the absorber.

7. The absorbent article according to claim 1, further comprising a support sheet that is coupled to the respective hanging parts of each of the pair of first and second floating leg gathers; and
a second transferring passage for bodily fluids is formed by the hanging parts and the support sheet.

8. The absorbent article according to claim 7, wherein parts where the support sheet is coupled to the respective hanging parts of the pair of first and second floating leg gathers are included in parts where the surface sheet is coupled to the respective hanging parts of the pair of first and second floating leg gathers.

9. The absorbent article according to claim 1, wherein the transfer passage for bodily fluids is provided at least in an area of the crotch part.

10. The absorbent article according to claim 1, wherein the transfer passage for bodily fluids is provided at least in an area of the front body.

11. The absorbent article according to claim 1, wherein the transfer passage for bodily fluids is provided at least in an area of the rear body.

12. The absorbent article according to claim 1, wherein the transfer passage for bodily fluids is continuously provided over respective areas of the front body, the crotch part and the rear body.

* * * * *